(12) United States Patent
Ha et al.

(10) Patent No.: US 10,369,058 B2
(45) Date of Patent: Aug. 6, 2019

(54) CONFORMABLE MEDICAL DRESSING WITH SELF SUPPORTING SUBSTRATE

(71) Applicant: 3M INNOVATIVE PROPERTIES COMPANY, St. Paul, MN (US)

(72) Inventors: Phong VanThanh Ha, Hudson, WI (US); Richard L. Jacobson, Stillwater, MN (US); Donald G. Peterson, Shoreview, MN (US); Karen M. St. Sauver, Maplewood, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 52 days.

(21) Appl. No.: 14/886,145

(22) Filed: Oct. 19, 2015

(65) Prior Publication Data

US 2016/0038345 A1 Feb. 11, 2016

Related U.S. Application Data

(62) Division of application No. 12/815,528, filed on Jun. 15, 2010, now Pat. No. 9,168,180.

(60) Provisional application No. 61/187,659, filed on Jun. 16, 2009.

(51) Int. Cl.
*A61F 13/00* (2006.01)
*A61F 13/02* (2006.01)

(52) U.S. Cl.
CPC ...... *A61F 13/0236* (2013.01); *A61F 13/0008* (2013.01); *A61F 13/00059* (2013.01); *A61F 13/00063* (2013.01); *A61F 13/02* (2013.01); *A61F 13/025* (2013.01); *A61F 13/0226* (2013.01); *A61F 13/0233* (2013.01); *A61F 13/0289* (2013.01); *A61F 2013/008* (2013.01); *A61F 2013/00165* (2013.01); *A61F 2013/00387* (2013.01); *A61F 2013/00412* (2013.01); *A61F 2013/00553* (2013.01); *A61F 2013/00578* (2013.01); *A61F 2013/00608* (2013.01); *A61F 2013/00825* (2013.01); *A61F 2013/00846* (2013.01)

(58) Field of Classification Search
USPC .......................... D24/189; 12/888, 889, 189
See application file for complete search history.

(56) References Cited

U.S. PATENT DOCUMENTS

| | | |
|---|---|---|
| 1,920,808 A | 8/1933 | Sander |
| 2,330,693 A | 9/1943 | Erdely |
| 2,367,690 A | 1/1945 | Purdy |

(Continued)

FOREIGN PATENT DOCUMENTS

| | | |
|---|---|---|
| DE | 298 20 217 | 6/1999 |
| DE | 10 2008 020554 A1 | 10/2008 |

(Continued)

OTHER PUBLICATIONS

U.S. Appl. No. 61/042,338, Scholz, filed Apr. 4, 2008.

(Continued)

*Primary Examiner* — Kim M Lewis
(74) *Attorney, Agent, or Firm* — 3M Innovative Properties Company; Trisha D. Adamson

(57) ABSTRACT

A medical dressing comprising a backing layer and a self-supporting substrate. The backing layers form a perimeter around the self supporting substrate and hold the self supporting substrate in place on a wound.

15 Claims, 7 Drawing Sheets

(56) References Cited

U.S. PATENT DOCUMENTS

| | | |
|---|---|---|
| 2,896,618 A | 7/1959 | Schaefer |
| RE24,906 E | 12/1960 | Ulrich |
| 3,194,235 A | 7/1965 | Cooke |
| 3,389,827 A | 6/1968 | Abere |
| D215,566 S | 10/1969 | Gilson |
| 3,528,416 A | 1/1970 | Chamberlain |
| 3,645,835 A | 2/1972 | Hodgson |
| 3,761,211 A | 9/1973 | Parkinson |
| 3,782,377 A | 1/1974 | Rychilk |
| 3,884,606 A | 5/1975 | Schrenk |
| 3,924,990 A | 12/1975 | Schrenk |
| 4,112,213 A | 9/1978 | Waldman |
| 4,212,296 A | 7/1980 | Schaar |
| 4,310,509 A | 1/1982 | Berglund et al. |
| 4,322,877 A | 4/1982 | Taylor |
| 4,323,557 A | 4/1982 | Rosso et al. |
| 4,328,441 A | 5/1982 | Kroeger, Jr. |
| 4,330,730 A | 5/1982 | Kurz et al. |
| 4,398,910 A | 8/1983 | Blake et al. |
| 4,405,402 A | 9/1983 | Quilliam |
| 4,472,480 A | 9/1984 | Olson |
| 4,485,809 A | 12/1984 | Dellas |
| 4,499,896 A | 2/1985 | Heinecke |
| 4,541,426 A | 9/1985 | Webster |
| 4,569,674 A | 2/1986 | Phillips et al. |
| 4,595,001 A | 6/1986 | Potter et al. |
| 4,598,004 A | 7/1986 | Heinecke |
| 4,600,001 A | 7/1986 | Gilman |
| 4,606,871 A | 8/1986 | Krueger |
| 4,627,138 A | 12/1986 | Tm |
| 4,641,641 A | 2/1987 | Strock |
| 4,641,643 A * | 2/1987 | Greer ............... A61L 15/58 128/888 |
| 4,664,106 A | 5/1987 | Snedeker |
| 4,667,666 A | 5/1987 | Fryslie |
| 4,737,410 A | 4/1988 | Kantner |
| 4,743,232 A | 5/1988 | Kruger |
| 4,778,446 A | 10/1988 | Jensen |
| 4,820,586 A | 4/1989 | Krueger |
| 4,969,880 A | 11/1990 | Zamierowski |
| 4,972,829 A | 11/1990 | Knerr |
| 5,088,483 A | 2/1992 | Heinecke |
| 5,100,396 A | 3/1992 | Zamierowski |
| 5,106,362 A | 4/1992 | Gilman |
| 5,153,859 A | 10/1992 | Chatigny |
| 5,160,315 A | 11/1992 | Heinecke et al. |
| 5,160,322 A | 11/1992 | Scheremet |
| 5,195,977 A | 3/1993 | Pollitt |
| 5,261,893 A | 11/1993 | Zamierowski |
| D347,058 S | 5/1994 | Valentine |
| 5,478,333 A | 12/1995 | Asherman, Jr. |
| 5,495,856 A | 3/1996 | Fentress |
| 5,527,293 A | 6/1996 | Zamierowski |
| 5,531,855 A | 7/1996 | Heinecke et al. |
| 5,562,107 A | 10/1996 | Lavender et al. |
| 5,622,711 A | 4/1997 | Chen |
| 5,633,010 A | 5/1997 | Chen |
| 5,702,356 A | 12/1997 | Hathman |
| 5,783,120 A | 7/1998 | Ouderkirk |
| 5,803,086 A | 9/1998 | Scholz et al. |
| 5,817,145 A | 10/1998 | Augustine et al. |
| 5,825,543 A | 10/1998 | Ouderkirk et al. |
| 5,851,549 A | 12/1998 | Svec |
| D409,754 S | 5/1999 | Dunshee |
| 5,979,450 A | 11/1999 | Baker et al. |
| 5,997,800 A | 12/1999 | Wimberger Friedl |
| 6,071,267 A | 6/2000 | Zamierowski |
| 6,107,536 A | 8/2000 | Dadinis |
| D430,674 S | 9/2000 | Dunshee |
| 6,143,216 A | 11/2000 | Loch et al. |
| 6,149,614 A | 11/2000 | Dunshee |
| 6,169,224 B1 | 1/2001 | Heinecke et al. |
| D437,217 S | 2/2001 | Bloor |
| 6,264,976 B1 | 7/2001 | Heinecke et al. |
| D454,955 S | 3/2002 | Dunshee |
| 6,420,622 B1 | 7/2002 | Johnston et al. |
| 6,436,432 B2 | 8/2002 | Heinecke |
| 6,461,467 B2 | 10/2002 | Blatchford et al. |
| D465,572 S | 11/2002 | Dunshee |
| D473,947 S | 4/2003 | Jacobson |
| 6,539,691 B2 | 4/2003 | Beer |
| 6,607,764 B1 | 8/2003 | Keller |
| 6,685,682 B1 | 2/2004 | Heinecke et al. |
| 6,733,803 B1 | 5/2004 | Vidkjaer |
| 6,742,522 B1 | 6/2004 | Baker et al. |
| D493,230 S | 7/2004 | Liedtke |
| 6,867,342 B2 | 3/2005 | Johnston et al. |
| 6,893,655 B2 | 5/2005 | Flanigan et al. |
| 6,913,803 B2 | 7/2005 | Peper |
| 6,916,967 B2 | 7/2005 | Wright et al. |
| 6,933,051 B2 | 8/2005 | Fleming et al. |
| 6,949,283 B2 | 9/2005 | Kollaja et al. |
| 6,994,904 B2 | 2/2006 | Joseph et al. |
| 7,179,245 B2 | 2/2007 | Glori |
| 7,183,454 B1 | 2/2007 | Rosenberg |
| 7,214,217 B2 | 5/2007 | Pedersen et al. |
| 7,216,651 B2 | 5/2007 | Argenta |
| 7,265,256 B2 | 9/2007 | Artenstein |
| D557,413 S | 12/2007 | Buermann |
| 7,429,687 B2 | 9/2008 | Kauth |
| 7,476,698 B2 | 1/2009 | Wagener et al. |
| D612,504 S | 3/2010 | Ha |
| 7,777,397 B2 | 8/2010 | Bharti |
| D629,910 S | 12/2010 | Ha |
| D629,911 S | 12/2010 | Ha |
| 7,994,383 B2 | 8/2011 | Zocher |
| 8,372,051 B2 | 2/2013 | Scholz et al. |
| 2002/0082540 A1 | 6/2002 | Johnston |
| 2003/0006669 A1 | 1/2003 | Pei et al. |
| 2003/0007038 A1 | 1/2003 | Nakatani |
| 2003/0097100 A1 | 5/2003 | Watson |
| 2003/0153965 A1 | 8/2003 | Supronowicz |
| 2004/0073151 A1 | 4/2004 | Weston |
| 2004/0109236 A1 | 6/2004 | Nishioka |
| 2004/0243073 A1 | 12/2004 | Lockwood |
| 2005/0046030 A1 | 3/2005 | Nakamura |
| 2005/0089539 A1 | 4/2005 | Sholz et al. |
| 2006/0051384 A1 | 3/2006 | Sholz et al. |
| 2006/0051385 A1 | 3/2006 | Sholz |
| 2006/0052452 A1 | 3/2006 | Sholz |
| 2006/0079852 A1 | 4/2006 | Bubb et al. |
| 2006/0147701 A1 | 7/2006 | Lockridge |
| 2007/0156075 A1 | 7/2007 | Heinecke |
| 2007/0172157 A1 | 7/2007 | Buchman |
| 2007/0209326 A1 | 9/2007 | Tretina |
| 2007/0233022 A1 | 10/2007 | Henley |
| 2008/0004559 A1 | 1/2008 | Riesinger |
| 2008/0033377 A1 | 2/2008 | Kauth |
| 2008/0091152 A1 | 4/2008 | Asherman |
| 2009/0299341 A1 | 12/2009 | Kazala, Jr. et al. |
| 2010/0286639 A1 | 10/2010 | Scholz |
| 2011/0106030 A1 | 5/2011 | Scholz |

FOREIGN PATENT DOCUMENTS

| | | |
|---|---|---|
| EP | 0 051 935 | 5/1982 |
| EP | 2 161 011 | 3/2010 |
| GB | 1 549 756 | 8/1979 |
| JP | S53-125781 | 10/1978 |
| JP | S57-120019 | 7/1982 |
| JP | 60090558 | 5/1985 |
| JP | 62133615 | 8/1987 |
| JP | 8-276537 | 10/1996 |
| JP | 2000-127176 | 5/2000 |
| JP | 2011-521739 | 7/2011 |
| WO | WO 83/03549 | 10/1983 |
| WO | WO 93/09727 A | 5/1993 |
| WO | WO 2002/096647 A2 | 12/2002 |
| WO | WO 03/011352 | 2/2003 |
| WO | WO 2006/048240 | 5/2006 |
| WO | WO 2006/118059 A1 | 11/2006 |
| WO | WO 2007/011596 | 1/2007 |
| WO | WO 2007/030598 | 3/2007 |
| WO | WO 2007/030601 | 3/2007 |

(56) References Cited

FOREIGN PATENT DOCUMENTS

| WO | WO 2008/014358 | 1/2008 |
|---|---|---|
| WO | WO 2008/015574 | 2/2008 |
| WO | WO 2008/019310 | 2/2008 |
| WO | WO 2008/041926 | 4/2008 |
| WO | WO 2009/066104 | 5/2009 |
| WO | WO 2009/067062 | 5/2009 |
| WO | WO 2009/088757 | 7/2009 |
| WO | WO 2009/124100 | 10/2009 |
| WO | WO 2009/124125 | 10/2009 |
| WO | WO 2009/015128 | 12/2009 |
| WO | WO 2009/158133 | 12/2009 |

OTHER PUBLICATIONS

U.S. Appl. No. 61/017,957, Scholz, filed Dec. 31, 2007.
U.S. Appl. No. 61/042,698, Bharti, filed Apr. 4, 2008.
U.S. Appl. No. 12/936,255, Bharti, filed Apr. 1, 2009.
U.S. Appl. No. 12/936,273, Scholz, filed Apr. 1, 2009.
Yoon, C-B., et al., "Multilayer Bender-Type PZT-PZN Actuator by Co-Extrusion Process," Journal of the European Ceramic Society, vol. 26 (2006) pp. 2345-2348.
*Handbook of Pressure Sensitive Adhesive Technology*, Van Nostrand-Reinhold, 1982, pp. 384-403, chapter 18.
International Search Report, PCT/US2010/038595, dated Jul. 30, 2010, 3 Pages.
Written Opinion of the International Searching Authority, PCT/US2010/038595, dated Jul. 30, 2010, 6 Pages.
International Search Report, PCT/US2008/088092, dated Mar. 27, 2009, 6 Pages.
Written Opinion of the International Searching Authority, PCT/US2008/088092, dated Mar. 27, 2009, 12 Pages.
International Search Report, PCT/US2008/052900, dated Jul. 28, 2008, 3 Pages.
Written Opinion of the International Searching Authority, PCT/US2008/052900, dated Jul. 28, 2008, 3 Pages.
International Search Report, PCT/US2009/039058, dated Jul. 9, 2009, 4 pages.
Written Opinion of the International Searching Authority, PCT/US2009/039058, dated Jul. 9, 2009, 6 pages.
International Search Report, PCT/US2009/039149, dated May 13, 2009, 3 pages.
Written Opinion of the International Searching Authority, PCT/US2009/039149, dated May 13, 2009, 7 pages.
Fleischmann, W. et al.; "Infektbehandlung durch Vakuumversiegelung"; Unfallchirurg; vol. 100; 1997; 4 pgs.
Thomas, S.; "An introduction to the use of vacuum assisted closure"; World Wide Wounds; 2001; 9 pgs.

* cited by examiner

CONFORMABLE MEDICAL DRESSING WITH SELF SUPPORTING SUBSTRATE

CROSS REFERENCE TO RELATED APPLICATIONS

This application is a divisional of U.S. patent application Ser. No. 12/815,528, filed Jun. 15, 2010 (now U.S. Pat. No. 9,168,180) which claims the benefit of U.S. Provisional Patent Application No. 61/187,659, filed Jun. 16, 2009, the disclosure of which are incorporated by reference herein in their entirety.

BACKGROUND OF THE INVENTION

Transparent film dressings are widely used as protective layers over wounds because they facilitate healing in a moist environment while acting as a barrier to contaminating liquids and bacteria. The films are also used as surgical drapes because of their barrier properties. Dressings and drapes fitting the above description are available under a number of trade names such as TEGADERM™ (3M Company, St. Paul, Minn.), BIOCLUSIVE™ (Johnson & Johnson Company, New Brunswick, N.J.), and OP-SITE™ (T. J. Smith & Nephew, Hull, England). The polymeric films used in those dressings and drapes are conformable, i.e., the films are extremely thin, flexible and supple. They are typically supplied with a releasable protective liner covering the adhesive coated surface of the film. When the liner is removed, the adhesive coated film tends to wrinkle and adhere to itself, interfering with the smooth, aseptic application of the dressing to a patient's skin. Various delivery systems have been proposed to address this problem such as those disclosed in U.S. Pat. No. 6,685,682. The use of a removable carrier, which does not require tearing of the film after it has been placed on the patient, avoids the problems described above. The carrier also aids in accurate placement of the dressing on a patient. Even with the carrier however, the dressings can be difficult to place on an irregular body surface, such as a joint (e.g., knee, elbow) or shoulder.

In addition, the length of time over which the medical dressings may remain in place over wounds may be limited by many factors. Among the factors that may limit the usable life of a medical dressing is the accumulation of fluids within the wound. Some medical dressings have included the use of negative pressure wound therapy in which fluids are removed from beneath the wound dressings without requiring removal of the dressings from the patient. Dressings adapted for delivery of negative pressure wound therapy (such as those described in, e.g., U.S. Pat. Nos. 4,969,880; 5,261,893; 5,527,293; and 6,071,267 (all to Zamierowski)) often have constructions that can compromise the sterility of the wound over which they are placed. These products often require a tube or wound drain that is introduced either through a multi-piece dressing or under a single piece dressing. In either case, it is difficult to obtain a good seal between the tube or wound drain and, during treatment, air can leak into the wound. That air can carry contamination into the wound and/or impair the effectiveness of the pressure-based therapy. These effects can be compounded by wounds on or around irregular surfaces, such as the knee, elbow, shoulders, heel, and ankle.

A need remains for a medical dressing that can be more effectively supported and/or more conformable for application to irregular surfaces, and particularly those associated with a joint, such as a knee, ankle or elbow, and particularly in wound therapy applications.

SUMMARY OF THE INVENTION

The present invention provides medical dressings having a thin, flexible backing layer on the periphery and a self-supporting substrate that facilitates application of the dressing. The medical dressing is constructed to have improved adhesion to irregular shaped surfaces, such as a knee, and to permit easy application to the irregular shaped surfaces. The medical dressing comprising the self-supporting substrate is well suited to position a foam or absorbent pad onto a concave or convex surface. For example, the medical dressing comprising the self-supporting substrate is suitable for applying to the knee or elbow, while maintaining an intact sterile perimeter around the medical dressing.

In a preferred embodiment, the medical dressings and medical dressing kits described herein can also be used to provide a ported medical dressing for placement over a wound or other body site where controlled fluid access is desired. That fluid access is preferably available without removing or otherwise disturbing the medical dressing. In particular, the controlled fluid access provided by medical dressings described herein may be useful to remove fluids from the wound (as in, e.g., negative or reduced pressure therapies), to provide one or more gases (e.g., oxygen, nitric oxide, ozone, etc.) to a wound site, to provide one or more liquids (e.g., saline, etc.), and/or to provide one or more active agents (e.g., carried in a liquid or gas) to a wound site.

In most implementations, the medical dressing comprises an adhesive layer on a backing layer. The backing layer further comprises an opening that forms a window in the backing layer. A self-supporting substrate is applied to the backing layer, and is configured to retain and deliver the medical dressing to a wound. The self-supporting substrate remains on the medical dressing after application of the medical dressing to the wound. In most embodiments, the self-supporting substrate is a molded or pre-formed substrate with a corrugated portion, allowing the dressing to be easily applied to convex surfaces and other non-planar surfaces. Optionally, an absorbent pad, a foam, or other wound treatment material is applied in the opening of the backing layer, within the cavity formed between the self supporting substrate and the wound.

In most embodiments, the medical self-supporting substrate is permanently attached to a major surface of the backing layer, either on the surface of the backing layer opposite the surface facing the wound, or between the backing layer and the adhesive layer or on the adhesive layer. In some embodiments, the self-supporting substrate can be releasably attached to the top of the backing layer.

In one aspect, a medical dressing. is provided, comprising a backing layer with a first major surface, a second major surface, and an opening through the backing layer to form a window; a self-supporting substrate comprising a first planar surface comprising a corrugated pattern on at least a portion of the first planar surface, at least one side wall at an angle between zero to one hundred eighty degrees to the first planar surface, and a second planar surface connected to the at least one side wall in the form of a flange; wherein the self supporting substrate is attached to the backing layer to enclose the window on at least one of the first major surface or second major surface of the backing layer.

In another aspect, a medical dressing is provided, comprising a backing layer having first and second major surfaces and a window forming an opening though the backing layer; an adhesive on the first major surface of the backing layer; and a self supporting substrate attached to the second major surface of the backing layer, wherein the self supporting substrate has a size and position on the backing such that the self supporting substrate encloses the window, and further wherein the self supporting substrate projects from the second major surface of the backing layer to form a cavity and wherein the self supporting substrate is substantially more rigid than the backing layer to facilitate handling of the dressing.

In another aspect, an adhesive medical article is provided, comprising: (a) a conformable backing having a first major surface and a second major surface, and an opening through the backing; (b) a pressure sensitive adhesive coated on at least a portion of the first major surface of the backing; (c) a carrier releasably attached to at least a portion of the second major surface of the backing; and (d) a self-supporting substrate comprising a first planar surface, and at least one side wall formed at an angle between zero to one hundred eighty degrees to the first planar surface, and a second planar surface connected to the at least side wall in the form of flange; wherein the self supporting substrate is attached to the backing to enclose the opening through the backing to form a window.

In another aspect. a method of assembling a medical article is provided, comprising (a) providing a backing layer comprising a conformable backing having a first major surface and a second major surface, and an opening through the backing layer to form a window; a first adhesive coated on at least a portion of the first major surface of the backing layer; a carrier releasably attached to at least a portion of the second major surface of the backing layer; a second adhesive coated on at least a portion of the second major surface of the backing layer proximate the perimeter of the window, and a liner releasably adhered to the second adhesive; (b) providing a self-supporting substrate comprising a first planar surface, and at least one side wall formed at an angle between zero to one hundred eighty degrees to the first planar surface, and a second planar surface connected to the at least side wall in the form of flange; and (c) attaching the self supporting substrate to the second adhesive on the backing layer to enclose the window in the backing layer.

In another aspect, a self supporting substrate is provided, comprising a first planar surface, at least one side wall at an angle from zero to one hundred eighty degrees to the planar surface, a second planar surface connected to the at least one side wall in the form of a flange, and a corrugated pattern on at least a portion of the planar surface, wherein the self supporting substrate is semi-rigid with a % elongation from 100% to 500% and a modulus from 10,000 to 400,000.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. The term "and/or" (if used) means one or all of the identified elements/features or a combination of any two or more of the identified elements/features.

The term "and/or" means one or all of the listed elements/features or a combination of any two or more of the listed elements/features.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE DRAWINGS

The invention will be further described with reference to the drawings, wherein corresponding reference characters indicate corresponding parts throughout the several views, and wherein.

Figure 1:
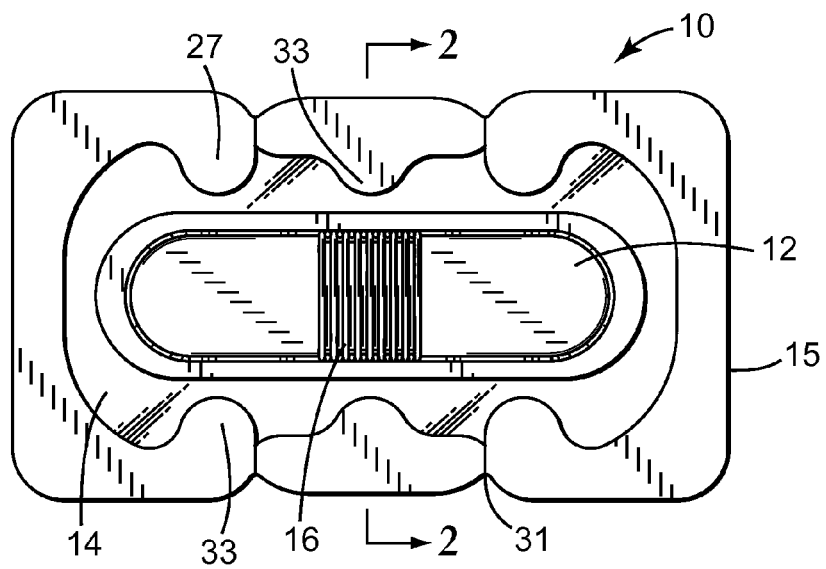
FIG. 1 is a top plan view of a medical dressing configured and arranged in accordance with one embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is directed to a medical dressing and self-supporting substrate, and methods of making the medical dressing and self-supporting substrate. The medical dressing and self-supporting substrate are particularly well suited to application over a convex surface of a patient, such as a patient's knee. The medical dressing permits a wound therapy, such as negative pressure therapy, to be located against the wound, while the self-supporting substrate aids in forming a seal around the convex or irregularly shaped area surrounding the wound.

In some implementations the medical dressing comprises a backing layer, an adhesive layer on the backing layer facing the wound, and a self supporting substrate. The adhesive layer and backing layer form a perimeter around the self supporting substrate and hold the self supporting substrate in place on a wound. The perimeter formed by the adhesive layer and backing layer keeps the self supporting substrate properly positioned, and also helps maintain a sterile environment around the wound. The adhesive layer and backing layer are typically extremely thin, and generally very flexible.

In most embodiments, the self-supporting substrate is permanently attached to the backing layer and remains on the medical dressing after the dressing is applied. The self-supporting substrate can be permanently attached to either side of the backing layer, e.g., the self-supporting substrate can be attached on the top of the backing layer or in less preferred embodiments, the self-supporting substrate may be attached on the side of the backing layer facing the wound. As used herein, "permanently attached" means that the self-supporting substrate cannot be removed from the backing layer without significantly damaging or destroying the backing layer, thereby rendering the medical dressing nonfunctional. The self-supporting substrate can be permanently attached to the backing layer directly or permanently attached by an attachment layer, such as an adhesive.

The medical dressing is highly conformable, and is easy and fast to apply to a wound site. There is no need to remove and dispose of the self-supporting substrate after the dressing is applied to the wound.

The medical dressings described herein can be used to provide a sealed environment over a wound or other body site. Fluid removed from the sealed environment may include gases and/or liquids (which may contain dispersed solid particles such as necrotic tissue, blood clots, etc.). The fluid removal can be performed through an opening in the dressing, such as a valve, without removing or otherwise disturbing the medical dressing.

As used herein, the term "sealed environment" means that fluids (and solids) from the ambient atmosphere surrounding the exterior of a medical dressing attached over a wound cannot freely enter the sealed environment. The sealed environment preferably includes a hermetic seal between the medical dressing and the surface surrounding the wound such that a negative pressure can be maintained in the sealed environment. It may, for example, be preferred that the medical dressing be capable of holding (at least temporarily as described herein) a vacuum of 100 mmHg (i.e., a pressure that is 100 mmHg below atmospheric pressure) and perhaps a vacuum as much as 200 mmHg Although some conventional medical dressings can provide such a sealed environment, the medical dressings of described herein can do so while also offering the opportunity to remove fluids (liquids and/or gases) from the sealed environment through an opening, such as a valve, provided as a part of the medical dressing.

As used herein, the term "self supporting" means that the substrate can hold a definable shape in the x-, y-, and z-plane in the absence of any applied force. In some embodiments, the substrate may withstand some level of applied pressure or force.

As used herein the term "vacuum" refers to pressures less than the surrounding atmospheric pressure. Preferably the pressure is reduced by 5-250 mm mercury (Hg) (e.g., down to an absolute pressure of 500-740 mmHg, but this will depend on the atmospheric pressure). When the pressure is reduced by more than 250 mmHg the patient may experience pain. Thus, preferably the pressure is not reduced by more than 200 mmHg and more preferably by not more than 175 mm Hg. Preferably, the pressure is reduced by at least 5 mmHg, 25 mmHg, more preferably at least 50 mmHg and most preferably at least 75 mm Hg in order to remove sufficient interstitial fluid.

Fluid removal from the sealed environment may be useful to provide negative or reduced pressure therapies to a wound over which the medical dressing is located. Fluid removed from the wound dressing may include gases and/or liquids (which may contain dispersed solid particles such as necrotic tissue, blood clots, etc.). The fluid removal can be performed without removing or otherwise disturbing the medical dressing. Without limitation on the generality of the useful applications of the present invention, the dressing may be applied over surgical wounds, cosmetic surgical procedures, burns, cuts, scrapes and ulcers of various types, e.g. diabetic, decubitus, peripheral vascular disease, venous stasis and trauma ulcers.

With the medical dressing and self supporting substrate described herein, the sealed environment created by a medical dressing of the present invention may preferably be maintained at a negative pressure (i.e., pressure below the ambient atmospheric pressure) in the absence of active vacuum source in fluid communication with the sealed environment. In other words, the medical dressings of the present invention may be used to maintain a sealed environment with a negative or reduced pressure in the periods between active removal of fluids from the sealed environment. As a result, the medical dressings can provide a negative or reduced pressure environment with only intermittent or periodic fluid removal.

Although the magnitude of the negative pressure maintained in the sealed environment by the medical dressings will typically deteriorate over time (after reaching a maximum during that active removal of fluids from the sealed environment), it may be preferred that the medical dressing be capable of maintaining the negative pressure for at least some significant period of time. In some embodiments, it may be preferred that the medical dressing be capable of maintaining at least some level of negative pressure in the sealed environment (in the absence of active fluid removal) for a period of 1 minute or more, 5 minutes or more, 10 minutes or more, 15 minutes or more, 30 minutes or more, or even 60 minutes or more.

Deterioration of the negative pressure within the sealed environment defined by the medical dressing may be caused by a variety of sources. For example, some of the deterioration may be due to the diffusion of gas into the sealed environment through the backing of the medical dressing and/or the adhesive attaching the medical dressing to a subject. Another source of negative pressure deterioration in the sealed environment may be caused by gases and/or liquids entering the sealed environment from the subject (i.e., through the wound itself and/or the tissue surrounding the wound).

Among the potential advantages that may be associated with use of the medical dressings of the invention is that, in some instances, the negative pressure may advantageously pull the edges of acute incisional wounds together, thus potentially providing faster healing, reduced infection rates, and/or improved cosmetic results (reduced scarring).

In one aspect, the present invention provides a medical dressing comprising a backing comprising an interior surface and an external surface; adhesive on at least a portion of the interior surface, wherein the adhesive extends around a perimeter of the interior surface of the backing to adhere the medical dressing to a subject over a wound; a self supporting substrate attached to the backing over an opening formed through the backing; wherein, when the medical dressing and self supporting substrate are attached over the wound, and preferably the medical dressing defines a sealed environment over the wound. In preferred embodiments, a vacuum applied to the backing, such as through a valve on the self-supporting substrate, allows fluid within the sealed environment to be removed through the opening in the backing.

In another aspect, the present invention may provide a medical dressing comprising a backing comprising an interior surface and an external surface; adhesive on at least a portion of the interior surface, wherein the adhesive extends around a perimeter of the interior surface of the backing to adhere the medical dressing to a subject over a wound; a self supporting substrate attached to the backing over an opening formed through the backing, wherein the self supporting substrate comprises a minimum thickness as measured normal to the interior surface and the external surface of the backing of 5 millimeters.

In another aspect, the present invention provides a medical dressing kit, the kit comprising a medical dressing according to any one of the embodiments provided above; optionally, a valve; optionally, a standoff element; optionally, a septum element; optionally, a closure element; optionally, a barrier element; optionally, wound packing material; optionally, a pump; optionally, a fluid trap; and optionally, a fitting adapted for attachment to the external surface of the backing over the valve.

In various embodiments, the methods may include one or more of the following features: applying a medical dressing over a wound according to any one of embodiments such as those provided herein; and removing fluid from the sealed environment through the valve in the medical dressing. In some embodiments such as those provided herein, the method of removing fluid from the internal volume comprises removal of air such that the pressure within the sealed environment is below atmospheric pressure; and the method of removing fluid from the internal volume comprises removal of wound exudate from the wound.

Although the medical dressings of the present invention may be used to provide negative pressure wound therapy, in some instances fluids or other materials may potentially be delivered into the sealed environment through the medical dressing. For example, delivery devices such as pipettes, needles, etc. may be used to pierce the backing of the medical dressing, with the fluids or other materials delivered into the sealed environment through the delivery devices. It may be preferred that the delivery of materials into the sealed environment through the medical dressing does not functionally compromise the ability of the medical dressing to define a sealed environment as described herein.

To provide resealable access to the sealed environment through the medical dressing, the material used for the medical dressing backing may, for example, be self-sealing such that the opening formed through the backing seals upon removal of the delivery device (in the manner of, e.g., a septum). In other instances, a closure element may be applied over the external surface of the medical dressing backing after the delivery device is removed to close any opening formed through the backing by the delivery device.

It is contemplated that fluids are delivered through the septum by inserting a tube similar to a vascular access catheter in which the catheter is inserted through the septum with the assistance of a blunt needle or introducer which is subsequently removed, leaving behind the blunt end relatively flexible catheter tubing. In this manner, no needle remains in place on the patient.

Fluids delivered to the sealed environment through the medical dressing may include gases (e.g., oxygen, nitric oxide, ozone, etc.) and/or liquids (e.g., saline, water, etc.). Particulates may, in some instances, also be delivered to the sealed environment if, e.g., they are entrained within a fluid delivered into the sealed environment.

Illustrative Exemplary Embodiments

FIG. 1 shows one embodiment of a medical dressing and self-supporting substrate as described herein. The medical dressing 10 includes a self supporting substrate 12. A backing layer 14 extends out to the perimeter 15 of the medical dressing 10. The backing layer 14 is typically extremely thin, flexible, and either transparent or translucent, allowing the wound and/or surrounding skin to be viewed through it.

Figure 2:
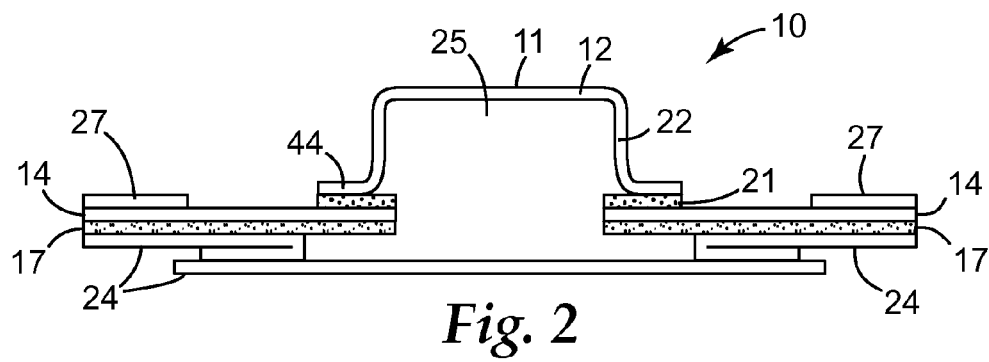
FIG. 2 is a schematic cross section of the medical dressing of FIG. 1.

FIG. 2 shows a schematic cross section of the medical dressing in FIG. 1 as viewed line 2-2 of the dressing 10 in FIG. 1. The backing layer 14 comprises an adhesive layer 17 on all or a portion of the surface of the backing layer 14 that faces the wound during use. The self-supporting substrate 12 is applied to the backing layer 14 on the top surface facing away from the wound. The self supporting substrate 12 in FIG. 2 also includes an adhesive layer 21. The adhesive layer 21 may be a single layer of adhesive, or may be an adhesive composite, such as an adhesive/polyethylene/adhesive composite. This adhesive layer 21 may facilitate attachment to the backing layer 14. The adhesive layer 21 can comprise the same materials used for adhesive 17. Preferably, adhesive layer 21 comprises a material that is compatible with the material used to make self supporting substrate 12.

Figure 7:
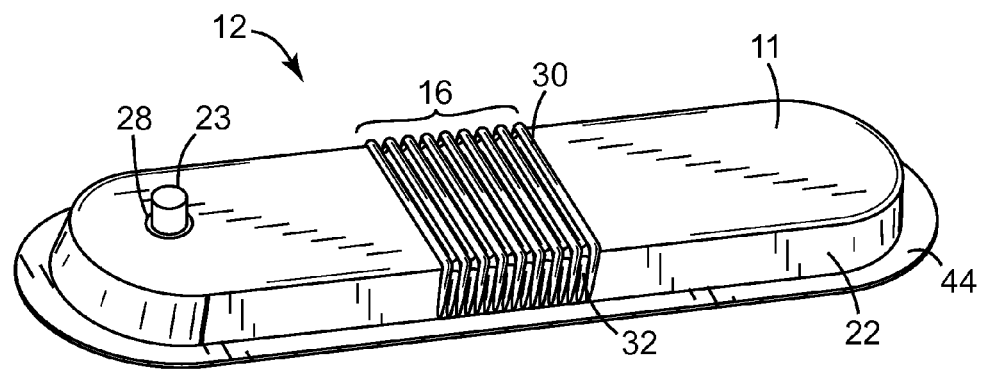
FIG. 7 is top perspective view of a self supporting substrate configured in accordance with one embodiment of the invention
Figure 8:
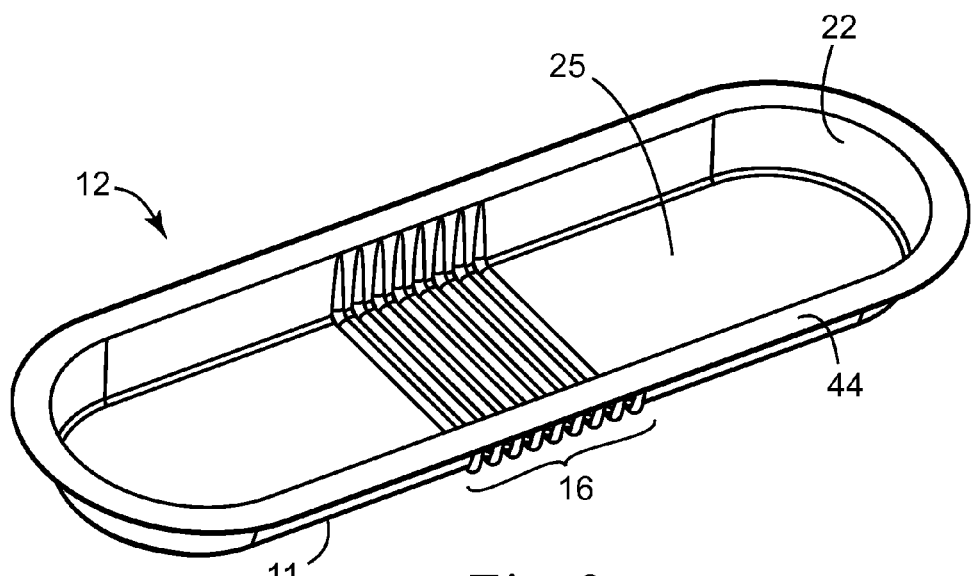
FIG. 8 is bottom perspective view of a self supporting substrate configured in accordance with one embodiment of the invention.

As shown in FIG. 2, the self supporting substrate 12 generally comprises a first planar surface 11, at least one side wall 22, and a flange 44. Flange 44 generally comprises a second planar surface that is generally parallel to the planar surface 11. The side wall 22 may be substantially continuous in a generally circular or oval pattern, such as shown in FIGS. 7-8. In alternate embodiments, more than one side wall may be formed, i.e., two or more side walls formed at angles to one another (not shown). The planar surface 11 and at least one side wall 22 form a cavity 25 enclosed within the profile of self supporting substrate 12 that projects from the backing layer 14. The flange 44 generally provides a planar surface that is used to attach the self supporting substrate 12 to the backing layer 14.

As shown in FIGS. 1 and 6-10, the self-supporting substrate 12 comprises a corrugated portion 16 on the planar surface 11 of the self supporting substrate 12. The corrugated portion 16 shown in FIGS. 1 and 6-10 comprises a portion of the planar surface 11 proximate the center of the planar surface 11. In alternate embodiments, the corrugated portion 16 may comprise a portion of the planar surface 11 at one end, or the entire surface of planar surface 11 may be comprised of the corrugated portion.

In FIGS. 1-9, the corrugated portion 16 is shown laterally over the shorter distance of the planar surface 11. In alternate embodiments, the corrugated portion may be in any direction, e.g. longitudinally or otherwise, that aids in the conformation of the medical dressing on an irregular surface.

The corrugated portion 16 aids in the conformability of the dressing 10 when applied to a patient. As the planar surface 11 of the self supporting substrate 12 is bent or rotated to conform to the wound surface, such as a knee, the corrugated portion 16 can expand to allow the self supporting substrate 12 to conform to the wound surface without flattening against the wound surface, or otherwise without compressing the wound surface and/or any intervening elements (e.g., a foam or wound packing material, or other elements as described below) in the cavity 25 of the self supporting substrate 12.

Figure 9:
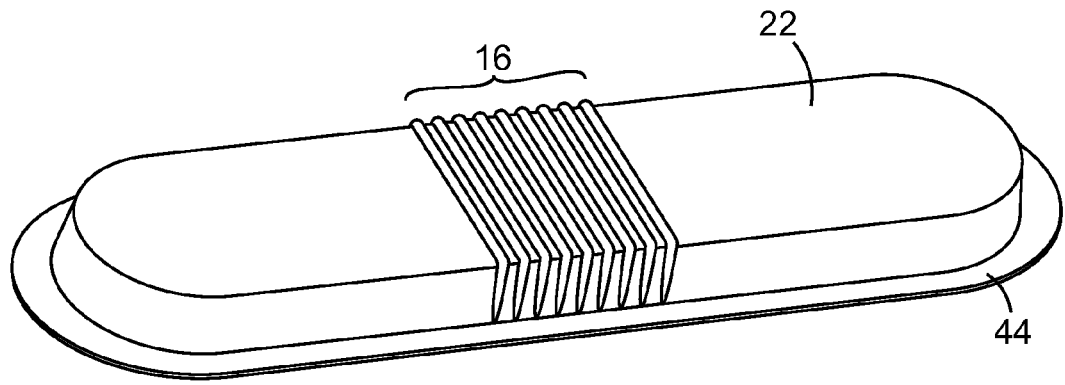
FIG. 9 is top perspective view of a self supporting substrate configured in accordance with another embodiment of the invention.
Figure 10:
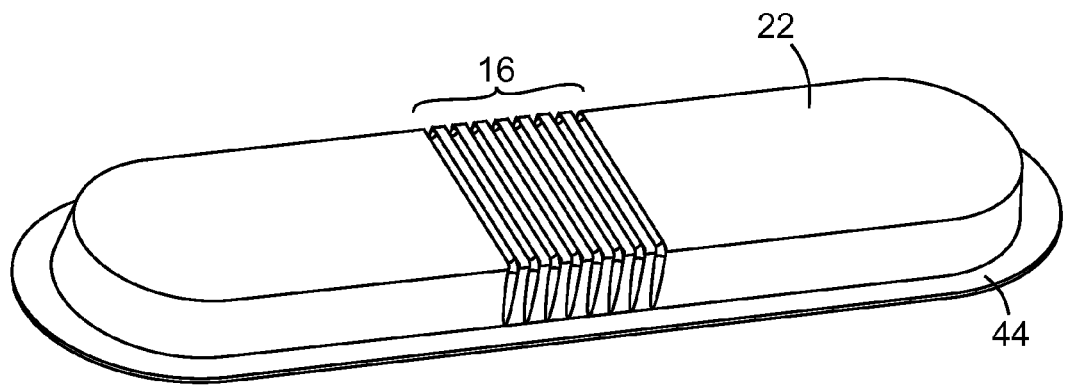
FIG. 10 is top perspective view of a self supporting substrate configured in accordance with another embodiment of the invention.

As shown in the FIGS. 1 and 6-10, the corrugated portion is formed from ridges and grooves. However, any pattern that creates available surface area may be used on the planar surface 11 of the self supporting substrate 12. For example, the pattern may comprise only ridges as shown in FIG. 8, or only grooves, as shown in FIG. 9. Additionally, rather than a parallel ridge/groove pattern, the ridges and/or grooves may form alternate patterns, such as a honeycomb or grid pattern.

The corrugated portion 16 provides additional surface area that can expand when the self supporting substrate 12 is bent or otherwise conformed around an irregular surface. In reference to the x-, y-, and z-plane, the corrugated portion 16 in the planar surface 11 of FIG. 1, when the ridges and grooves of the corrugated portion 16 run parallel to the y-axis, and when the planar surface 11 in the x-axis is bent around the y-axis, the ridges of the planar surface 11 expand along the x-axis as the planar surface 11 is bent toward the z-axis without compression of the self supporting substrate 12 in the z-axis. In other words, the self supporting substrate 12 can expand along the radius of the bend without compressing the ridges and/or grooves of the corrugated portion 16.

Self supporting layer 12 can be a single piece of material, such as a nonwoven material or a polymeric film, or can be two or more distinct pieces. In a preferred embodiment, self supporting substrate 12 is translucent or transparent.

As shown in FIG. 2, the medical dressing 10 typically includes a release liner 24. The release liner 24 covers the surface of the medical dressing applied to the patient during use, generally making contact with at least a portion of the adhesive layer 17. The release liner 24 remains attached to medical dressing 10 until a user is ready to apply the dressing. The release liner 24 may be a single piece or multiple piece release liner, and may be part of or laminated to the package (not shown) containing the dressing, or merely enclosed along with the dressing within the package. The release liner 24 keeps the adhesive 17 clean during storage and shipping of the medical dressing 10. Once the release liner 24 and dressing 10 are separated, only a carrier 27 (as described further below) and self supporting substrate 12 provide significant rigidity to the backing layer 14.

Figure 3:
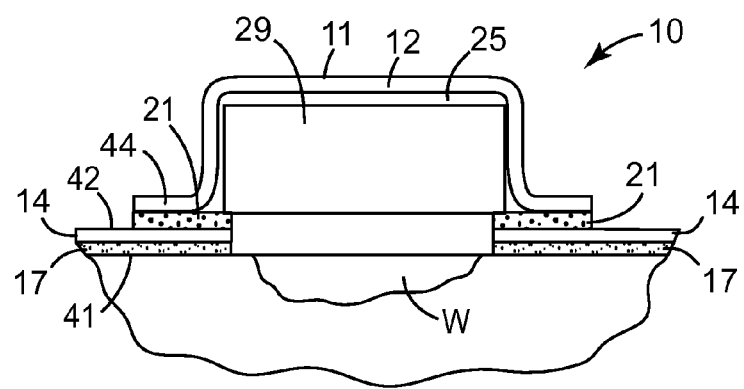
FIG. 3 is a schematic cross section of the medical dressing of FIG. 1 applied to a wound.

Another embodiment of a medical dressing according to the present invention is depicted in FIG. 3 (where FIG. 3 is a cross-sectional view taken along line 2-2 in FIG. 1). The medical dressing 10 includes a backing 14 (which may preferably be conformable as described herein). The backing 14 includes two opposed major surfaces: an interior surface 41 and an external surface 42. In use, the interior surface 41 faces a wound (or other body site) over which the dressing is placed while the external surface 42 faces away from the wound (or other body site).

Potentially suitable materials for the backing 14 are described in more detail below, but functionally, the backing 14 is preferably made of materials that serve as a barrier to both liquid and rapid gas diffusion. The barrier properties of the backing 14 may or may not be absolute, e.g., the backing 14 may allow for limited passage of gas, although the backing 14 (and the other components of the dressing 10) preferably provide sufficient barrier properties to the passage of gas such that, when placed over a wound, a negative pressure environment can be at least temporarily maintained above a wound. For example, the backings may preferably have relatively high moisture vapor transmission rates, but be substantially impervious to liquids.

The dressing 10 may include a valve 23 on opening 28 in self supporting substrate 12 (as shown in FIG. 7). Fluid flow through the one or more openings 28 in the backing 14 maybe controlled by valve 23. Valve 23 (which may preferably be a one-way valve) may be used to provide negative pressure therapy to a wound over which the dressing 10 is placed as described herein. Although the medical dressing includes only one opening 28 for the valve, medical dressings of the present invention may include more than one valve if additional access to the sealed environment defined by the dressing is desired.

The dressing 10 may also include an adhesive 17 on the interior surface 41 such that the dressing 10 can be adhered to a subject over a wound with the interior surface 41 facing a wound. The adhesive 17 may cover all or part of the interior surface 41 in a continuous and/or pattern coated fashion. The dressing 10 also includes a wound packing or barrier element 29 (as described further below). Many other arrangements are possible, including dressings that are secured without the need for pressure sensitive adhesives. For example, the dressing may comprise a circumferential wrap around a limb which would not necessarily require an adhesive.

Figure 4A:
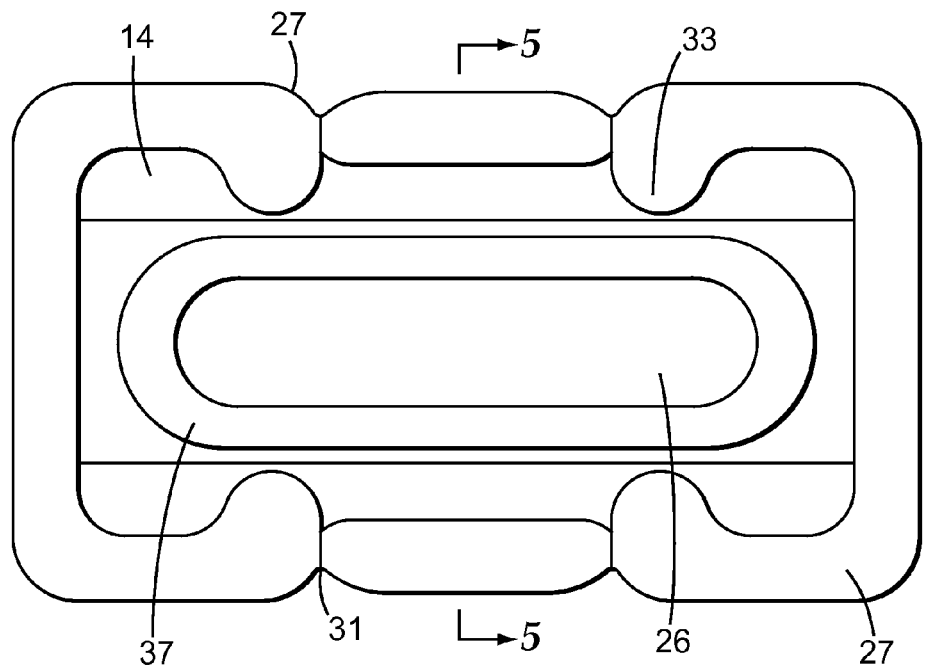
FIG. 4A is a top plan view of an exemplary embodiment of a medical dressing prior to the addition of a self supporting substrate.
Figure 4B:
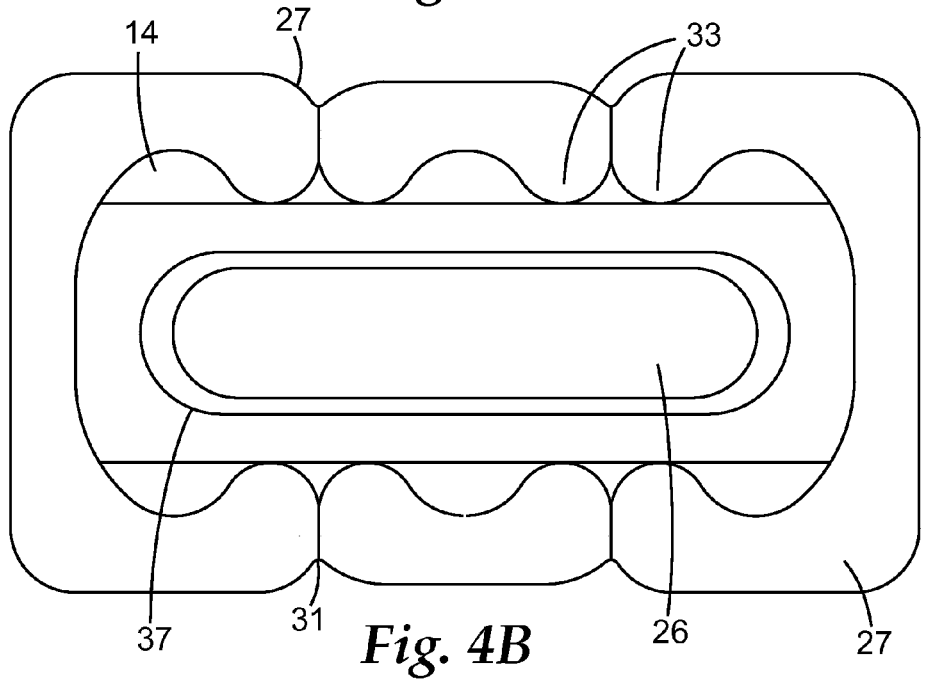
FIG. 4B is a top plan view of another exemplary embodiment of a medical dressing prior to the addition of a self supporting substrate.

As shown in FIGS. 4A-4B, the backing layer 14 further comprises an opening that forms a window 26 through the backing layer 14.

Referring again to FIG. 3, the dressing 10 is located over a wound W while the backing layer 14 and adhesive layer 17 is attached to the tissue (e.g., skin) surrounding the wound W. The dressing 10 and self supporting substrate 12, along with the wound W and the tissue surrounding the wound, preferably define a sealed environment in which the wound W is isolated from the surrounding environment. The interior surface 41 of the backing 14 faces the sealed environment in which the wound is located while the external surface 42 of the backing 14 faces away from the wound W.

The adhesive 17 as depicted in FIGS. 1-3 may preferably be exposed on all of the interior surface of the backing 14. In any embodiment, however, it may be preferred that the adhesive 17 extend continuously around the entire perimeter of the backing 14 such that the dressing 10, when attached to a subject, can form a sealed environment over a wound.

Returning to FIGS. 4A-4B and 5, in the portion of the dressing prior to attachment of the self supporting substrate 12, preferred embodiments of the backing layer 20 comprise a backing 14 which is preferably conformable as described above; a pressure-sensitive adhesive (not shown) on a bottom face of the backing 14; a liner 24 attached to the exposed surface of pressure-sensitive adhesive; an optional low adhesion coating on the top face of the backing; a carrier 27 attached to the top face of the backing 14; one or more cut lines 31 traversing the carrier 27; one or more tabs 33 to aid in removal of carrier 27; opening or window 26; and window liner 37.

In the preferred embodiment, the carrier 27 is attached to backing 14 with a heat seal bond. The heat seal bond between the carrier 27 and the backing 14 is stronger than the bond between the adhesive and the liner 24. That difference ensures that the backing 14 remains attached to the carrier 27 when liner 24 is removed from the adhesive composite dressing 10. In other embodiments, the carrier can be adhesively attached to backing 14.

Carrier 27 can include a linear cut 31 that traverses the entire surface of the carrier 27 in at least one direction. The linear cut 31 may be provided in the cross-web or down-web direction.

The linear cut 31 can provide a tab 33 that creates a beginning point at which the carrier 27 may be easily lifted from backing 14 and peeled. Although cut 31 may also be a nonlinear cut which is known in the art, the preferred embodiment includes a linear cut. Linear cuts form a more distinct tab 33 to facilitate removal of the carrier 27. Tab 33 can also be formed away from the linear cut 31 as a shape in carrier 27, as shown in FIG. 4B.

Figure 5:
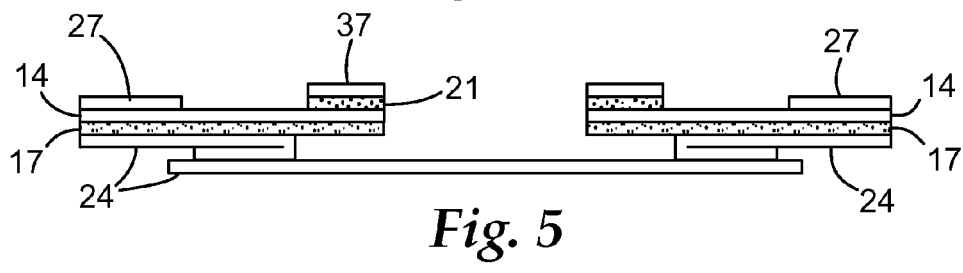
FIG. 5 is a schematic cross section of the medical dressing of FIGS. 4A-4B.
Figure 6:
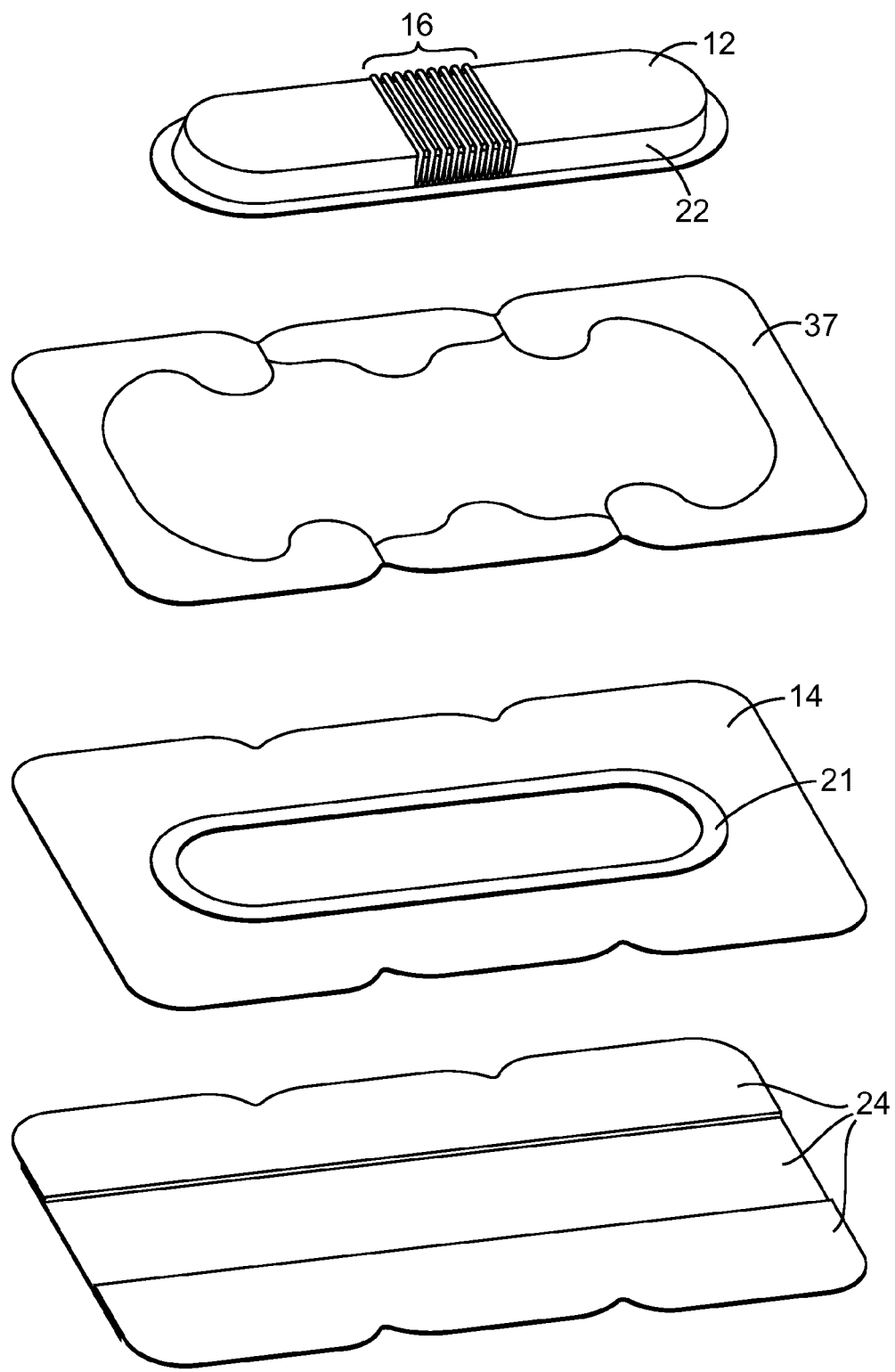
FIG. 6 is an exploded perspective view of a medical dressing configured and arranged in accordance with one embodiment of the invention.

In FIG. 6, an exploded view of the dressing 10 as shown in FIGS. 1-2 depicts the adhesive layer 21 that can be used to attach self supporting substrate 12 to the backing layer 14. In a preferred embodiment, the liner 37 in FIGS. 4-5 is removed to expose the adhesive 21. A self supporting substrate 12 is then attached to backing 14 with adhesive 21. In an alternate embodiment (not shown), the self supporting substrate 12 may be directly bonded to the backing layer 14.

The adhesive 21 as depicted in FIG. 6 is provided only around the perimeter of the window 26 on the exterior surface of the backing 14 such that the adhesive 21 forms a frame around the opening of the window 26 on the exterior surface 22 of the backing 14.

As shown in FIG. 7, the self supporting substrate 12 also comprises an opening 28, for access to the dressing during fluid removal or application, such as through a valve. Although only one opening 28 is shown in FIG. 7, multiple openings may also be employed in the dressings described herein. With the use of a suitable valve, although not required, the sealed cavity 25 (shown in FIG. 8) created by the self supporting substrate 12 of dressing 10 attached over a wound may preferably be maintained at a negative pressure (i.e., pressure below the ambient atmospheric pressure on the external surface 42 of the backing 14, as shown in FIG. 3) in the absence of active vacuum source in fluid communication with the sealed cavity 25.

Referring again to FIG. 3, maintenance of the negative pressure within the sealed environment may, in some embodiments, be enhanced by the addition of a ballast component 29 within the sealed cavity 25 created by the self supporting substrate 12. A ballast component 29 may be a resiliently compressible material that, e.g., compresses or shrinks as a vacuum (negative pressure) is provided within the sealed cavity 25 and that attempts to return to at least a portion of its pre-compression size because of its resilient nature. For example, the ballast component 29 may be a resilient foam (open or closed cell, although preferably open cell), nonwoven material, spring, or other structure that can be compressed, but that also is resilient such that it will attempt to return to at least a portion of its pre-compressed size (e.g., the resilient material has a spring constant).

It may be preferred that the valve used in connection with the present invention be capable of being used one, two or more times to remove fluids from the sealed cavity 25 without requiring that the medical dressing 10 be removed and without requiring the constant removal of fluid to maintain a negative pressure within the sealed environment. For example, fluid can be removed from the sealed cavity 25 through the opening 28 as described herein, with the valve being allowed to close when the fluid removal terminates. As additional fluid accumulates in the sealed environment, it can be removed through the valve as described herein.

In some embodiments, it may be preferred that the medical dressing include absorbent material to absorb fluids (e.g., liquids) entering the sealed environment. Examples of potentially suitable absorbent materials may include, but are not limited to, hydrophilic foams, woven materials, nonwoven materials, etc. and combinations thereof. It may be preferred that the absorbent material be both absorbent and capable of releasing at least some (preferably a majority) of any absorbed fluids when a vacuum is applied to the sealed environment through a valve. By releasing absorbed fluids during the removal of fluids from the sealed environment, the ability of the absorbent material to absorb fluids may be regenerated—which may prolong the useful life of the medical dressing.

Although the magnitude of the negative pressure maintained in the sealed environment by the dressing 10 will typically deteriorate over time (after reaching a maximum during that active removal of fluids from the sealed environment through the opening 28), it may be preferred that the dressing 10 be capable of maintaining the negative pressure for at least some significant period of time. In some embodiments, it may be preferred that the dressing 10 be capable of maintaining at least some level of negative pressure in the sealed environment (in the absence of active vacuum source) for a period of 1 minute or more, 5 minutes or more, 10 minutes or more, 15 minutes or more, 30 minutes or more, or even 60 minutes or more.

Deterioration of the negative pressure within the sealed environment defined by the dressing 10 may be caused by a variety of sources. For example, some of the deterioration may be due to the diffusion of gas into the sealed environment through the backing 14 and/or the adhesive 17 attaching the backing 14 to the subject. Another source of negative pressure deterioration in the sealed environment may be caused by gases and/or liquids entering the sealed environment from the subject (through the wound itself and/or the tissue surrounding the wound).

One exemplary embodiment of a valve that may be used in a medical dressing 10 as described herein is found in FIGS. 4A-4C of Applicants International Publication No. WO2009/124125, and incorporated by reference in its entirety. Although this valve represents one embodiment of a potentially suitable valve that may be used in connection with the present invention, many other valves may be used in place of the specific valve structure depicted in FIGS. 4A-4C.

The pressure differential across the valve may be achieved by, e.g., applying the inlet of a pump (e.g., a vacuum pump) or a fluid conduit (e.g., tube, hose, etc.) leading to the inlet of a pump over the external surface of valve on the external surface 42 of the backing 14. The pump is preferably capable of providing a reduced pressure environment on the external side of the valve such that the pressure differential across the valve is high enough to reach the cracking pressure. Once the valve is in the open configuration, fluids (gases and/or liquids) in the sealed environment defined by the dressing 10 over the wound may be removed through the opening 28 and valve. The fluids removed from the sealed environment may or may not contain solid particles.

It may be preferred that the fluid removal place the sealed environment at a negative pressure as discussed herein, although such a condition is not necessarily required. For example, the fluid removal may be limited to removing fluids such as wound exudate, blood, etc. from the sealed environment without necessarily resulting in a negative pressure condition within the sealed environment.

Various other implementations are appropriate in order to add or take away from the aspects shown in FIGS. 1-9. For example, the backing layer 14 can be multiple films or coatings without diverging from the invention or deviating from the meaning of the term "film" as used herein. Similarly, the self supporting substrate 12 can include multiple sub-layers, including films, webs, sheets, etc. Also, additional layers and films of other materials can be added between the materials described herein without deviating from the invention.

The medical dressing 10 is typically applied to a patient by first cleaning the wound and making sure the area around the wound is ready to receive a dressing. The release liner is then removed from the dressing, exposing the opening or window 26 in the backing layer, the perimeter of the adhesive layer 17 and the backing layer 14. This perimeter of the backing layer 14 is maintained in a generally planar or stretched orientation by the carrier 27. The self supporting substrate that encloses the window 26 in the backing layer 14 is placed over with the wound, and then the edges of the dressing 10 are gently and smoothly pressed against the patient, thereby bringing the exposed adhesive perimeter of the backing layer 14 in contact with the patient.

In certain embodiments, adhesive layer 17 is provided on one major surface of the backing layer 14 in order to make it adhesive, and a low adhesion coating (low adhesion backsize or LAB) can be provided on the other major surface of the backing layer 14. The low adhesion coating reduces the need to change the dressing 10 due to unwanted dressing removal when other tapes or devices are placed on the dressing 10 and removed, and reduces the surface friction of the dressing 10 on linen or other fabrics, thereby offering additional protection against the accidental removal of dressing 10. A description of a low adhesion backing material suitable for use with the present invention can be found in U.S. Pat. Nos. 5,531,855 and 6,264,976, which are compatible with a heat seal bond described below, and are incorporated herein in their entirety.

In addition, it will also be appreciated that any of the dressings of the present invention may include additional tape strips or other structures useful for securing devices (e.g., tubes, catheters) to a patient, as described in U.S. Pat. No. 5,160,315, the disclosure of which is herein incorporated by reference.

Any of the above embodiments may also comprise one or more of the following elements in any combination: wound packing material, a pump, and/or a fluid trap, valves, stand-off elements to provide open fluid pathways to the valves (that resist closing under negative pressure in the sealed environment), barrier elements (to limit clogging of the valves); septum elements, and/or closure elements, as described in Applicants International Publication Nos. WO2009/124125; WO2009/088757 and WO2009/124100.

Additional aspects of various components of the invention will now be described in greater detail.

Backing Materials

The wound dressings of the present invention are useful in connection with any conformable backing that provides a sufficiently impermeable barrier to the passage of liquids and at least some gases. Representative backings may include non-woven and woven fibrous webs, knits, films, foams polymeric films and other familiar backing materials. The preferred backing materials include thin elastomeric backings. These types of backings help ensure conformability and high adhesion around the wound site. Preferred backing materials may be translucent or transparent polymeric films including polyurethanes (e.g. ESTANE), polyether polyesters (e.g. HHTREL), polyether amides (e.g. PEGAX) as well as polyolefins (e.g. ENGAGE).

Suitable backing materials for the backing layer include, for example, nonwoven fibrous webs, woven fibrous webs, knits, films and other familiar backing materials. The backing materials are typically translucent or transparent polymeric elastic films. The backing can be a high moisture vapor permeable film backing. U.S. Pat. No. 3,645,835 describes methods of making such films and methods for testing their permeability.

The backing advantageously should transmit moisture vapor at a rate equal to or greater than human skin. In some embodiments, the adhesive coated backing layer transmits moisture vapor at a rate of at least 300 g/m$^2$/24 hrs/37° C./100-10% RH, frequently at least 700 g/m$^2$/24 hrs/37° C./100-10% RH, and most typically at least 2000 g/m$^2$/24 hrs/37° C./100-10% RH using the inverted cup method.

The backings used in connection with the present invention may be high moisture vapor permeable film backings. Issued U.S. Pat. Nos. 3,645,835 and 3,645,835 describe methods of making such films and methods for testing their permeability. The film (and any adhesive used thereon as described herein) may transmit moisture vapor at a rate equal to or greater than human skin. The adhesive-coated film may, e.g., transmit moisture vapor at a rate of at least 300 g/m$^2$/24 hrs/37° C./100-10% RH, more preferably at least 700 g/m$^2$/24 hrs/37° C./100-10% RH, and most preferably at least 2000 g/m$^2$/24 hrs/37° C./100-10% RH using the inverted cup method as described in U.S. Pat. No. 4,595,001.

The backing layer is generally conformable to anatomical surfaces. As such, when the backing layer is applied to an anatomical surface, it conforms to the surface even when the surface is moved. The backing layer is also conformable to animal anatomical joints. When the joint is flexed and then returned to its unflexed position, the backing layer typically stretches to accommodate the flexion of the joint, but is resilient enough to continue to conform to the joint when the joint is returned to its unflexed condition.

A description of this characteristic of backing layers preferred for use with the present invention can be found in issued U.S. Pat. Nos. 5,088,483 and 5,160,315, the disclosures of which are hereby incorporated by reference. As discussed, particularly preferred backings are elastomeric polyurethane, polyester, or polyether block amide films. These films combine the desirable properties of resiliency, high moisture vapor permeability, and transparency found in preferred backings.

The backings may also preferably be conformable to anatomical surfaces. As such, when the backing is applied to an anatomical surface, it conforms to the surface even when the surface is moved. The backing may also be conformable to animal anatomical joints. When the joint is flexed and then returned to its unflexed position, the backing may stretch to accommodate the flexion of the joint, but is resilient enough to continue to conform to the joint when the joint is returned to its unflexed condition. A description of this characteristic of backings can be found in issued U.S. Pat. Nos. 5,088,483 and 5,160,315. Examples of some potentially suitable backings may include elastomeric polyurethane, polyester, or polyether block amide films. These films combine the desirable properties of resiliency, high moisture vapor permeability, and transparency.

Commercially available examples of potentially suitable backing materials may include the thin polymeric film backings sold under the tradenames TEGADERM (3M Company), BIOSITE (Johnson & Johnson Company), OPSITE (Smith & Nephew), etc. Many other backings may also be used, including those commonly used in the manufacture of surgical incise drapes (e.g., incise drapes manufactured by 3M Company under the tradenames STERIDRAPE and IOBAN), etc.

Because fluids may be actively removed from the sealed environments defined by the medical dressings of the present invention, a relatively high moisture vapor permeable backing may not be required. As a result, some other potentially useful backing materials may include, e.g., metallocene polyolefins and SBS and SIS block copolymer (e.g., KRATON type) materials could be used.

Regardless, however, it may be preferred that the backings be kept relatively thin to, e.g., improve conformability. For example, it may be preferred that the backings be formed of (e.g., consist essentially of) polymeric films with a thickness of 200 micrometers or less, or 100 micrometers or less, potentially 50 micrometers or less, or even 25 micrometers or less.

Self Supporting Substrate

In most embodiments, the self supporting substrate is a thermoplastic polymer. The preferred polymer is polyethylene.

Thermoplastic materials suitable for use as the self supporting substrate include, for example, polyolefins (such as polyethylene); natural and synthetic rubbers (for example, styrene butadiene rubber or butyl rubber, polyisoprene, polyisobutylene, polybutadiene, polychloroprene, acrylonitrile/butadiene as well as functionalized elastomers such as carboxyl or hydroxyl modified rubbers, and the like); silicones including but not limited to polydimethylsiloxanes; styrenic block copolymers (for example, styrene-isoprene-styrene or styrene-ethylene/butylene-styrene block copolymer); polyurethanes including but not limited to those based on aliphatic isocyanate and aromatic isocyanate; and combinations thereof. Thermoset polymers may also be used.

In most embodiments, the self supporting substrate 12 is translucent or transparent. In preferred embodiments, the thermoplastic materials are semi-rigid with a % elongation from 100% to 500% and a modulus from 10,000 to 400,000. Materials outside these parameters may not hold the shape of the self supporting substrate once formed.

The material used to form the self supporting substrate is generally substantially more rigid than the backing layer. In preferred embodiments, the thickness of the material is less than 6 mil, more preferably less than 5 mil. In most embodiments, the substrate material thickness is greater than 1 mil. In general, the self supporting substrate materials can include, but are not limited to, an elastic film, a non-elastic film, non-woven fibrous web, woven fibrous web, knits, and polyethylene/vinyl acetate copolymer-coated papers and polyester films.

The self-supporting substrate adhered or attached to the backing layer either directly or by an adhesive layer. The self supporting substrate can be pre-formed, such as by a mold process, then attached the dressing 10 as shown in FIG. XX, e.g., by laminating the self supporting substrate with an adhesive layer 21 to the backing layer 14. The self-supporting substrate can also be laminated to the adhesive layer 17 to attach the self supporting substrate to the backing layer 14 on the surface of the backing later facing the wound (not shown).

Other ways of attaching the self-supporting substrate include irreversible heat bonding or ultrasonically welding of the self-supporting substrate to the backing layer. The self-supporting substrate can be attached on the top of the backing layer, between the backing layer and the adhesive layer, or attached to the adhesive layer.

A self supporting substrate can be formed from a mold or other formed structure to form the desired construction. In one embodiment, a polyethylene film can be held between two plates with a designated open area. The polyethylene film is heated above its softening point but below its melting point. A plunger optionally with the desired corrugated shape can be pushed into the softened film to a depth that corresponds with the desired profile of the self supporting substrate. After the polyethylene film cools below its softening point, the plunger is removed. The formed self-supporting substrate is cut around a determined edge of plate to include the second planar surface used to attach the self supporting substrate to the dressing.

Pressure Sensitive Ashesive

Suitable adhesive for use in wound dressing articles of the present invention include any adhesive that provides acceptable adhesion to skin and is acceptable for use on skin (e.g., the adhesive should preferably be non-irritating and non-sensitizing). Preferred adhesives are pressure sensitive and in certain embodiments preferably have a relatively high moisture vapor transmission rate to allow for moisture evaporation. Suitable pressure sensitive adhesives include those based on acrylates, polyurethanes, KRATON and other block copolymers, silicones, rubber based adhesives (including natural rubber, polyisoprene, polyisobutylene, butyl rubber etc.) as well as combinations of these adhesives. The adhesive component may contain tackifiers, plasticizers, rheology modifiers as well as active components including for example an antimicrobial agent.

The pressure sensitive adhesives that may preferably be used in the wound dressings of the present invention may include adhesives that are typically applied to the skin such as the acrylate copolymers described in U.S. Pat. No. RE 24,906, particularly a 97:3 isooctyl acrylate:acrylamide copolymer. Another example may include a 70:15:15 isooctyl acrylate: ethyleneoxide acrylate:acrylic acid terpolymer, as described in U.S. Pat. No. 4,737,410 (Example 31). Other potentially useful adhesives are described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310,509 and 4,323,557.

The pressure sensitive adhesives may, in some embodiments, transmit moisture vapor at a rate greater to or equal to that of human skin. While such a characteristic can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001. Other potentially suitable pressure sensitive adhesives may include blown-micro-fiber (BMF) adhesives such as, for example, those described in U.S. Pat. No. 6,994,904. The pressure sensitive adhesive used in the wound dressing may also include one or more areas in which the adhesive itself includes structures such as, e.g., the microreplicated structures described in U.S. Pat. No. 6,893,655.

Issued U.S. Pat. Nos. 3,645,835 and 4,595,001, the disclosures of which are hereby incorporated by reference, describe methods of making such films and methods for testing their permeability. Preferably, the film/adhesive composite should transmit moisture vapor at a rate equal to or greater than human skin. Preferably, the adhesive coated film transmits moisture vapor at a rate of at least 300 g/m²/24 hrs/37° C./100-10% RH, more preferably at least 700 g/m²/24 hrs/37° C./100-10% RH, and most preferably at least 2000 g/m²/24 hrs/37° C./100-10% RH using the inverted cup method as described in U.S. Pat. No. 4,595,001. While such a characteristic can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001, which is hereby incorporated by reference.

The preferred pressure sensitive adhesives which can be used in the adhesive composites of the present invention are the adhesives which are typically applied to the skin such as the acrylate copolymers described in U.S. Pat. No. RE 24,906, the disclosure of which is hereby incorporated by reference, particularly a 96:4 isooctyl acrylate:acrylamide copolymer. Also preferred is an 70:15:15 isooctyl acrylate: ethyleneoxide acrylate: acrylic acid terpolymer, as described in U.S. Pat. No. 4,737,410 (Example 31), the disclosure of which is hereby incorporated by reference. Other useful adhesives are described in U.S. Pat. Nos. 3,389,827; 4,112,213; 4,310,509; and 4,323,557; the disclosures of which are hereby incorporated by reference. Inclusion of medicaments or antimicrobial agents in the adhesive is also contemplated, as described in U.S. Pat. Nos. 4,310,509 and 4,323,557 both of which are hereby incorporated by reference.

Absorbent Materials

An absorbent material may also be used in conjunction with the medical dressings described herein. An absorbent material may be the same as the wound packing material (described below) or may be a separate element. The absorbent materials can be manufactured of any of a variety of materials including, but not limited to, woven or nonwoven cotton or rayon. Absorbent pad is useful for containing a number of substances, optionally including antimicrobial agents, drugs for transdermal drug delivery, chemical indicators to monitor hormones or other substances in a patient, etc.

The absorbent may include a hydrocolloid composition, including the hydrocolloid compositions described in U.S. Pat. Nos. 5,622,711 and 5,633,010, the disclosures of which are hereby incorporated by reference. The hydrocolloid absorbent may comprise, for example, a natural hydrocolloid, such as pectin, gelatin, or carboxymethylcellulose (CMC) (Aqualon Corp., Wilmington, Del.), a semi-synthetic hydrocolloid, such as cross-linked carboxymethylcellulose (X4ink CMC) (e.g. Ac-Di-Sol; FMC Corp., Philadelphia, Pa.), a synthetic hydrocolloid, such as cross-linked polyacrylic acid (PAA) (e.g., CARBOPOL™ No. 974P; B.F. Goodrich, Brecksville, Ohio), or a combination thereof. Absorbent materials may also be chosen from other synthetic and natural hydrophilic materials including polymer gels and foams.

Carriers/Delivery Systems:

In some instances, the backings used in the medical dressings of the present invention may be so flexible and supple such that when a release liner is removed from the backing, the backing may tend to fold and adhere to itself, interfering with the smooth, aseptic application of the dressing to a patient's skin.

Various delivery systems have been proposed to address this problem such as those disclosed in U.S. Pat. Nos. 4,485,809; 4,600,001; and EPO Publication No. 0 051 935. Carrier-type delivery systems such as those described in U.S. Pat. No. 6,685,682 offer an alternative delivery system for use with conformable backings.

Alternative carriers and/or delivery systems may include frames, handles, stiffening strips, etc. as disclosed in issued U.S. Pat. Nos. 6,742,522; 5,979,450; 6,169,224; 5,088,483; 4,598,004; D 493,230; etc. Still another potentially suitable delivery system may be described in U.S. Patent Application Publication No. 2007/0156075 A1. In some instances, the backings can be delivered linerless as described in, e.g., U.S. Pat. No. 5,803,086.

The carrier material used to supply the carriers for dressings manufactured according to the present invention is preferably more rigid than the backing to prevent the backing from wrinkling during application. The carrier material can also be heat-sealable to the backing, with or without the low adhesion coating described below, for the purpose of manufacturing the preferred dressings. In general, the preferred carrier materials can include, but are not limited to, ethylene vinyl acetate copolymer or ethylene acrylic acid coated papers and polyester films.

The backing layer optionally also include a low adhesion coating on a top face of the backing, which is coated as a solution of polyvinyl N-octadecyl carbamate and a blend of silicone resins, as described in U.S. Pat. No. 5,803,086, which is incorporated by reference herein. It will also be understood that other coatings providing the low adhesion characteristics of the preferred coating could be substituted. The primary considerations in choosing any low adhesion coatings according to the present invention are their release characteristics and their compatibility with the attachment means between the carrier and the backing.

When the carrier is heat seal-bonded to the backing, the preferred low adhesion coating is compatible with the heat seal bond between the carrier and the backing and also retains its low adhesion characteristics after heat sealing. While it is preferred that the top face of the backing layer include a low adhesion coating, backing layers without such a coating with a carrier material attached thereto are also considered to be within the present invention.

Release Liners

Release liners may be supplied with the medical dressings of the present invention to protect the pressure sensitive adhesive used to attach the dressings to the patient and create the sealed cavity. Release liners that may be suitable for use in the medical dressing of the present invention can be made of supercalendered kraft paper, glassine paper, polyethylene, polypropylene, polyester or composites of any of these materials.

The liners are preferably coated with release agents such as fluorochemicals or silicones. For example, U.S. Pat. No. 4,472,480 describes low surface energy perfluorochemical liners. The liners may preferably be in the form of papers, polyolefin films, polyolefin coated paper or polyester films coated with silicone release materials. Examples of commercially available silicone coated release liners are POLY SLIK™ silicone release on polyolefin coated papers, FL2000™ silicone release on film, and STICK-NOT™ silicone release on supercalendered kraft paper, all available from Loparex Inc., (Willowbrook, Ill.); silicone coated supercalendered kraft paper from Akrosil, (Menasha, Wis.); and silicone release film from Huhtamaki Forchheim, (Forchheim, Germany). Another potential liner is silicone coated (1630) low density polyethylene available from Huhtamaki.

The selection of a specific release liner may be made in conjunction with the selection of a pressure sensitive adhesive. Those skilled in the art will be familiar with the processes of testing a new adhesive against different liners or a new liner against different adhesives to arrive at the combination of qualities desired in a final product. The considerations pertinent to the selection of a silicone release liner can be found in Chapter 18 of the *Handbook of Pressure Sensitive Adhesive Technology*, Van Nostrand-Reinhold, 1982, pp. 384-403. U.S. Pat. No. 4,472,480 also describes considerations pertinent to the selection of a perfluoropolyether release liner.

Valves

The valves provided in connection with the medical dressings of the present invention preferably have a relatively low profile or height. The low profile of the valves preferably reduces the likelihood that the medical dressing will be disturbed by external forces (from, e.g., bedding, clothing, etc.). The low profile valves may also improve patient comfort where, for example, the dressing is placed in a location on which the patient's weight rests while sitting, lying, and/or standing.

To retain a negative pressure within the sealed environments, it may be preferred that the openings in the medical dressings be one-way valves. In other words, it may be preferred that the valve allows fluid flow in one direction (out of the sealed environment) and restricts or prevents flow in the opposite direction (into the sealed environment). Alternatively, the valve allows fluid flow in one direction (into the sealed environment) and restricts or prevents flow in the opposite direction (out of the sealed environment).

Many valves can be used in the medical dressings described herein. For example, valves such as those known as "Goglio" type or "Raackmann" type valves may be used in connection with the present invention. Goglio-type valves are available, for example, from Bosch, Wipf, and Wico; Raackmann-type valves are available, for example, from Amcor. Other potentially suitable valves may include duckbill or umbrella valves (examples of which are those available from Vernay Laboratories, Inc., Yellow Springs, Ohio). Still other examples of suitable vacuum valves may include those described in U.S. Pat. Nos. 6,913,803; 6,733,803; 6,607,764; and 6,539,691, each of which is incorporated herein by reference in its entirety.

Barrier Elements

Another optional element that may be included with the medical dressings of the present invention are barrier elements that may be placed proximate the valves of the medical dressings. The barrier elements may preferably function to filter materials from wound exudates that may otherwise cause the valves to become contaminated such that the valves do not re-close or seal after fluids are removed from the sealed environments defined by the medical dressings. The barrier elements may be provided attached to the medical dressings (e.g., within the cavity of the self supporting substrate) or they may be provided with the medical dressings in an unattached form such the barrier elements can be placed during delivery of the medical dressings to a patient. Examples of some materials that may be filtered by the barrier elements may include, e.g., clotted blood, loose tissue, wound packing, etc.

The barrier elements may be provided using a variety of different materials. Examples of some potentially suitable materials for the barrier elements may include, e.g., fabrics (e.g., gauze, nonwoven fabrics, woven fabrics, knitted fabrics, etc.), foams, etc. The barrier elements may also potentially incorporate absorbent materials such as, e.g., hydrogels, hydrocolloids, etc. In some embodiments, the barrier elements may be resiliently compressible, such that the barrier elements can also optionally function as ballast components to assist in maintaining a negative pressure in the sealed environment as described herein.

Septem Element

In still other embodiments, a septum element may be attached to the medical dressing backing to provide resealable access to the sealed environment through the medical dressing (e.g. a septum). The medical dressing can include only one or more than one septum element. The septum elements may, in some embodiments, be found on only one side of the backing or on both sides of the backing. In still other embodiments, one or more pairs of septum elements may be located on both the interior surface and the external surface of the backing, directly opposed from each other.

Medical Dressing Kits

The medical dressings of the present invention may potentially be supplied in the form of a kit with one or more of the optional components. The kit may preferably be provided in a sealed package (e.g., bag, pouch, tray, etc.). The kit includes one or more medical dressings as described herein.

The kit may also include one or more pumps that can be used in conjunction with the medical dressings. The kit may also include one or more traps that may be used with the one or more pumps to retain fluids (e.g., liquids) that may be removed from sealed environments defined by the dressings over wounds. In other embodiments, the kits may include one or more fluid traps, but no pumps where, for example, the user has a reusable pump that can be used with the trap or traps supplied in the kit with the dressings. The kits may also potentially include one or more fittings adapted for attachment to the external surfaces of the dressings as discussed herein, where the fittings can be used to provide connections between the valves in the dressings and the pumps.

Active Agents

The medical dressing may optionally include at least one of a number of actives including for example, medicaments, anti-infective agents, antimicrobials, antiseptics (for example polyhexamethylene biguanide (hereinafter, "PHMB"), chlorhexidine, silver, iodine, an iodophor, benzalkonium chloride, hydrogen peroxide as well as the antiseptics disclosed in the following pending applications: US 2005/0089539, US2006/0051385, US2006/0052452, and US2006/0051384 which are incorporated herein by reference), antibiotics, analgesics, local anesthetics, anti-inflammatory agents, healing factors, vitamins, growth factors, enzyme inhibitors such as matrix metalloproteinase (MMP) inhibitors, and nutrients and/or one of a microbead packing and/or absorbent foam. Such actives may be introduced by elution off of any portion of the wound dressing including the backing, adhesive or porous filter, or from a separate storage chamber that allows controlled introduction of the medication into the wound space due to the reduced pressure environment. Alternatively, medication may be introduced as taught in U.S. Pat. No. 6,867,342 or by injecting the medication directly through the dressing.

In some instances, it may be desirable to deliver one or more active agents to the sealed cavity formed by the self supporting substrate (and, thus, the wound covered by the dressing). The active agents may be provided as a fluid and/or may be carried within a fluid that is delivered to the internal volume. Some potentially suitable active agents may include, e.g., antimicrobials, antibiotics, analgesics, healing factors such as vitamins, growth factors, nutrients and the like. Examples of other potentially suitable agents may be described in U.S. Pat. No. 6,867,342.

If delivered, an active agent (or agents) could be supplied to the sealed cavity continuously or intermittently. For example, an active agent could be delivered to the sealed cavity and allowed to remain in place (i.e., resident) for a selected period of time (e.g., several hours) followed by, e.g., delivery of a second active agent, delivery of negative pressure therapy, etc. The initial active agent could be removed before delivery of the second agent or it could be allowed to remain in place. Alternatively, the sealed cavity could be rinsed with, e.g., saline or another flushing solution before placing the sealed environment in a negative pressure condition, before delivery of a second agent, etc.

Wound Pumps

As discussed herein, the medical dressings of the present invention may be used for negative pressure wound therapy by providing an opening or port, such as a valve, in the medical dressing through which fluid can be removed from a sealed environment defined by the medical dressing. The fluid can be removed from the sealed environment using a pump that can preferably be periodically attached to the medical dressing. It may be preferred that the pump include a seat that can seal against the external surface of the backing of the medical dressing to provide a fluid-tight seal.

The pumps used in connection with the medical dressings of the present invention may take any suitable form. In some embodiments, the pumps may be portable, self-contained devices, while in other embodiments the pumps may be fixed, stationary systems. In some instances, fluids may even be removed from a sealed environment defined by the medical dressings using suction developed by a person using their mouth (in, e.g., a battlefield or other remote location). In one embodiment the pump is a pump as disclosed in Applicant's International Publication No. WO2009/124100.

Examples of some potentially suitable pumps that may be used with and/or supplied in a kit with the medical dressings of the present invention may include the pumps described in U.S. Patent Application Publication No. U.S. 2007/0209326 (Tretina), although many other pumps may be used in place of the pumps disclosed therein. Although the pumps described in the document identified above include a power source (e.g., a battery), pumps used in connection with the present invention may be manually powered. Examples of some other potentially suitable manually powered pumps may include, e.g., devices that include resilient cavities that can be compressed and, when returning to their pre-compression states, provide a vacuum force at the inlet of the pump (e.g., bulbs, hemovacs, etc.).

In some embodiments, the pumps may preferably include one or more traps or fluid collection components capable of collecting and retaining liquids (and, in some embodiments, gases) removed from the sealed environments defined by the medical dressings. The traps may be integral with the pumps in some embodiments, while in other embodiments the traps may be separate from the pumps such that the traps may be replaced without requiring replacement of both the pumps and the traps. Examples of some potentially suitable traps that are designed to separate liquids from the removed fluids may be described in, e.g., U.S. Patent Application Publication Nos. U.S. 2007/0209326 (Tretina) and U.S. 2007/0172157 (Buchman).

It may be preferred that the medical dressings of the present invention and any pumps used therewith to remove fluids from sealed environments be capable of quickly connecting with each other to form a fluid-tight seal during removal of fluids from the sealed environments defined by the medical dressings. The medical dressings and pumps may include more conventional connections/fittings to provide a fluid-tight connection between the pumps and the medical dressings. Such fittings may be useful where, e.g., the pump is to be connected to the medical dressing for an extended period of time, e.g., for more than 2 minutes. In such an embodiment, the medical dressing kit may include a fitting that attaches to the external surface of the backing using, e.g., a pressure sensitive adhesive, etc. The fitting may, for example, include a tubing connector, Luer lock fitting, etc. designed for longer-term connection to a pump. The adhesive used to attach the fitting to the medical dressing may be releasable, i.e., the fitting may potentially be removed from the dressing while the dressing remains in place over a wound, such that any sealed environment defined by the medical dressing remains intact during removal of the fitting.

In some embodiments, the pump is a low cost disposable pump. Disposing of the pump with each dressing change reduces the risk of bacterial contamination of the wound and transmission to other patients.

A check valve or other means may be required to regulate pressure, particularly for pumps able to create a vacuum of more than 100 mmHg below atmospheric pressure. This may be accomplished via a check valve that opens at a predetermined pressure drop and allows air into the wound bed. If a check valve is used it preferably has a membrane element that will filter out microorganisms and prevent them from entering the wound bed. Alternatively and preferably the pump is equipped with a pressure sensor and a control circuit that slows the pump speed at a predetermine pressure set point. The set point is preferably variable and easily set by the clinician. A read out of the pressure may be desired.

Alternatively, the pump is self limiting and unable to create a vacuum more than the desired maximum vacuum, e.g. more than about 150 mmHg.

The pump may be driven by AC or DC power and may be from a line or battery source. Preferably the pump is driven by a small disposable battery source. The power source may be located in a package with the pump or it may be at a remote site and connected to the pump.

The pump is preferably programmable to pull a continuous, intermittent or variable vacuum. For example, the pump could be programmed to pull and hold a vacuum of 100 mmHG or be programmed to pull a vacuum of 150 mmHg for a period of time following by a period of time at a vacuum of 25 mmHg below atmospheric pressure in an oscillatory fashion.

In a preferred embodiment, the pump is secured directly to the wound dressing either through the interior portion of the dressing or at the periphery. In either case an inlet tube may be unnecessary. The pump also can be remote from the dressing and attached via an inlet tube. In such case, the pump may have multiple inlets and exit ports and/or multiple pumps may be employed on a single dressing. Such inlet means may be a simple tube which passes fluid from the wound bed into the pump. The inlet of the inlet tube may then need to be protected by a porous filter element. The inlet means may be a simple flexible tube or may be other means such as the fluid control articles described in U.S. Pat. No. 6,420,622 or the drain tubes described in U.S. Pat. No. 6,420,622.

The pump exit is preferably in fluid communication with a reservoir designed to collect the excess wound fluid. The fluid reservoir may be a vented rigid container, a flexible container, or a vented flexible container. Preferred fluid reservoirs can be a flexible pouch similar to those used in ostomy appliances such as those disclosed in U.S. Pat. No. 7,214,217. The pouches may even be flushable as disclosed in U.S. Pat. No. 7,179,245. However, the fluid reservoir may be as simple as a vacuum canister such as used routinely in surgery, a canister such as described in U.S. Pat. No. 4,569,674. The collection pouch can be constructed of any suitable polymeric material but is preferably an odor barrier such as disclosed in U.S. Pat. No. 7,270,860. Furthermore, the collection reservoir may have a means for alerting the patient or care giver that it should be changed. This alert can be an electronic means or a passive means.

A sample port may be provided between the pump and the fluid reservoir or on the reservoir itself for easily obtaining a sample for analysis. For example, a "T" shaped tubing may be provided in the exit line or a simple valved port on the fluid reservoir with a lure lock for attaching a syringe may be used. The sample can be used for analysis of chemical or physical properties of the wound fluid in order to assess healing or for further treatment means.

Wound Packaging Material

In some embodiments, the medical dressings may be provided with wound packing material in place of a barrier element or in addition to a barrier element. The wound packing material may, in some embodiments, also function as a barrier element as described herein (although this function is not required). In some embodiments, the wound packing material may be resiliently compressible, such that the wound packing material can also optionally function as a ballast component to assist in maintaining a negative pressure in the sealed environment as described herein. For example, when a vacuum is applied the resilient packing will be compressed. When the vacuum is removed and the valve closed to seal the wound cavity the resilient packing will still provide an expansion force in order to return to its non-compressed state. This expansion will serve to create or help maintain a vacuum for a period of time.

Wound packing materials may be useful where, e.g., the wound to be contained within the sealed environment is a chronic wound that is in the form of a significant depression (which may, in some instances be tunneled under the surrounding skin). When treating such wounds, it may be desirable to provide wound packing material in the wound before applying a medical dressing to create a sealed environment over the wound.

The wound packing material may preferably be flexible such that it can fill and/or conform to the shape of the wound. The wound packing may be absorbent or non-absorbent. The wound packing may preferably be capable of providing passageways through which fluids can pass. Some potentially suitable examples of wound packing materials may include fully or partially reticulated foam (e.g., open cell polyurethane foams, etc.), fabric (e.g., gauze, mesh, woven, knit, or nonwoven materials), particulate materials, beads, etc. that may be placed in a wound to fill the internal volume. If provided in particulate or bead form, the particulates or beads may, in some embodiments, be contained within a flexible bag or other structure to facilitate removal of the wound packing (unless, e.g., the wound packing material is bioabsorbable and/or biodegradable). A preferred polyurethane foam may be hydrophilic and capable of spontaneously absorbing deionized water such as WILSORB foam (available from Illbruck). Preferred hydrophilic packing components will absorb a 100 microliter drop of deionized water when gently placed in contact with the foam in less than 60 seconds and preferably in less than 30 seconds.

Polyvinylalcohol (PVA) open cell foams may also be used. A preferred fabric is nonwoven fabric and more preferably a lofted nonwoven fabric having resiliency such that when compressed to 50% of its thickness rebounds to 90% or greater of the original thickness in less than 10 seconds and preferably in less than 1 second. A preferred lofted resilient nonwoven has physical properties similar to 3M Buff Puff™ Facial Sponge. These structures may be treated to be hydrophilic and spontaneously wet with water. In some preferred embodiments the intermediate material may include several hydrophilic colloid materials to absorb fluids. In other embodiments the intermediate layers are preferably hydrophobic in order to retard tissue ingrowth. One skilled in the art will appreciate that there may be a number of materials suitable for the intermediate layer to achieve various objectives including combinations of the materials mentioned above and combinations that include other materials.

The wound packing can be secured directly to the dressing. For example, the wound packing can be secured via the adhesive layer. In this embodiment the wound packing is placed at least over the portion of the dressing, and may be located where the pump inlet conduit will be located. This may be in the interior of the dressing or may be located at the periphery.

If the barrier element and/or wound packing materials are provided in a form such that they are not attached to the medical dressing, the medical dressing may be provided in the form of a kit including the medical dressing and the separate barrier element and/or wound packing. In using such a kit, the barrier element and/or wound packing may be attached to the medical dressing before the medical dressing is delivered to a patient. Alternatively, the barrier element and/or wound packing may be placed on or in the wound, with the medical dressing deployed over the wound after the barrier element and/or wound packing is/are in position.

Preferred Methods of Manufacture

In the preferred method, the carrier material is die cut to form the windows which lie in the center of the carriers on the preferred dressings. In the preferred embodiments, the die cutting is accomplished using rotary die cutting equipment which is well known to those skilled in the art. After the windows have been die cut in the carrier material, they are optionally removed. Removal of the windows defines the inner edge of the frame of carrier material which is located around the perimeter of each of the preferred dressings.

The windows die cut into the carrier material can be removed using a number of methods known to those skilled in the art. Those methods could include the use of vacuum, air pressure, gravity, and nip rolls having a small diameter which cause the windows to be removed from the framed carrier material.

As discussed above, the carrier material forming the window (which is removed) is preferably not heat sealed to the backing as is the remainder of the carrier material making up the frame of each dressing.

After the low adhesion coating step and the die cutting and window removal steps are completed, the carrier material (with windows removed) is preferably heat sealed to the top face of the backing, over the low adhesion coating.

Additional control over the heat sealing process can be accomplished a number of ways. It can include cavities in the heated rolls used in heat sealing or other means, such as texturing the nip rolls which compress the adhesive composite web against the heated roll during processing. Methods of manufacture that may be used with the carrier material are further described in U.S. Pat. No. 5,531,855.

Figure 11:
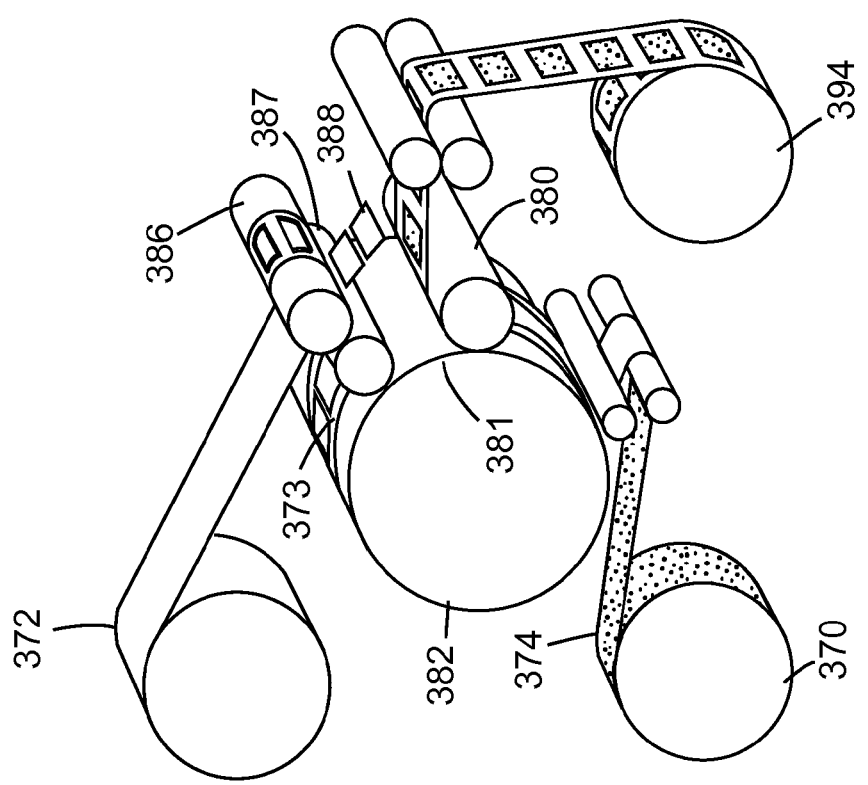
FIG. 11 is a portion of an exemplary process for manufacturing the medical dressing configured and arranged in accordance with one embodiment of the invention.
Figure 12:
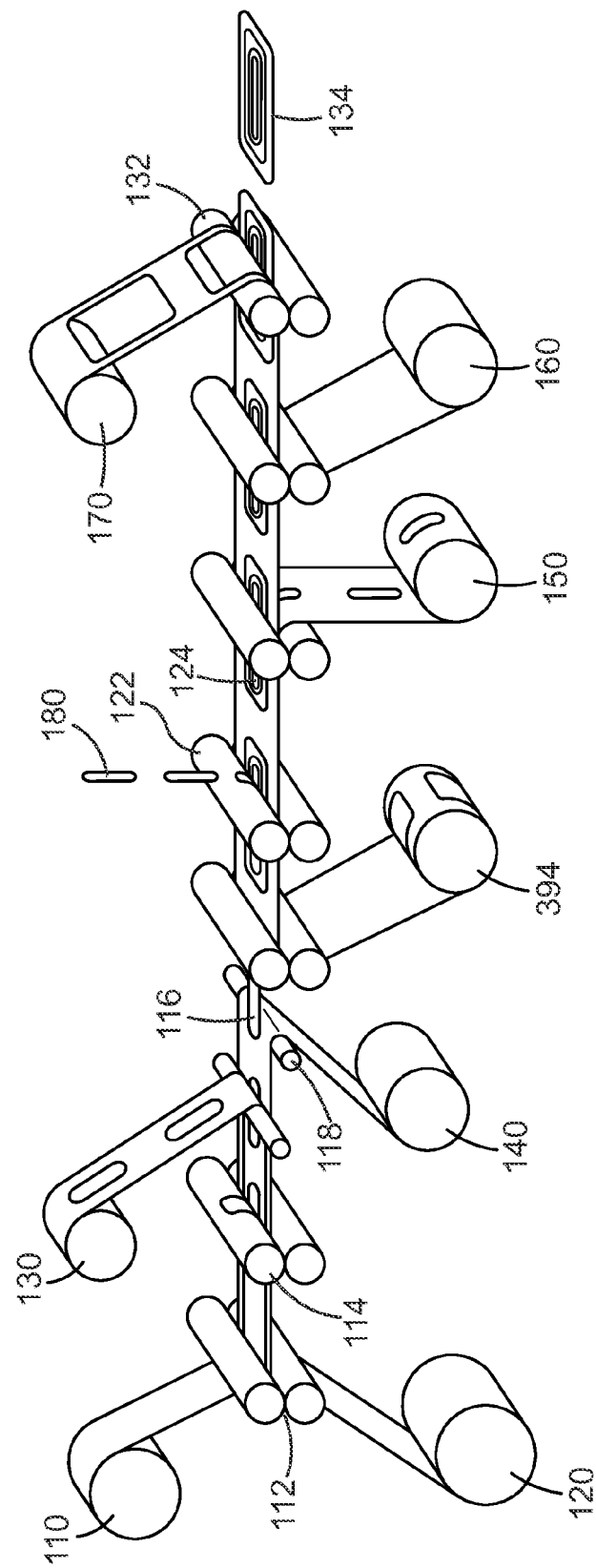
FIG. 12 is a portion of an exemplary process for manufacturing the medical dressing configured and arranged in accordance with one embodiment of the invention.

FIGS. 11-12 depict an exemplary process for manufacturing the medical dressings described herein. Turning to FIG. 11 for the first step in the process, roll 372 preferably comprises a heat sealable carrier material (also designated 372) as described above with the heat seal side 373 threaded as shown. The carrier material 372 is threaded between anvil roll 387 and a die cut roll 386. The die cut roll 386 and the anvil roll 387 die cut the carrier to form windows in the carrier material 372. The windows 388 are then removed using a variety of means as discussed above. The carrier material 372 is then rolled around a heated roll 382.

The second input roll 370 comprises the film/adhesive/waste liner composite (also designated 370). The film portion 374 is wound out and the liner 378 is wound in as shown. The web from input roll 370 is threaded between the nip 381 formed between the nip roll 380 and heated roll 382. Roll 394 is the output roll of the first step of the process.

As a second step, a first input roll 110 comprises an adhesive liner. Roll 110 is unwound and laminated to a liner 120 through nip 112. This liner/adhesive/liner is control depth die cut with die 114 through the top liner and adhesive, but not through the liner 120. Waste 130 is removed from the liner 120, leaving discrete adhesive/liner sections 116 spaced on the liner 120.

Roll 394 produced in this process step shown in FIG. 11 is unwound and the discrete liner/adhesive sections 116 are transferred from the liner 120 to the web from roll 394 over a peel bar 118 at matched web speed and in register to the web from roll 394 (designated as web 394). Web 394 is die cut with die 122 through the laminated portion of web 116 to produce an opening 124 and the slug 180 is removed from the web. The web 394 passes through a nip and laminate liner 150 is removed. Product liner(s) 160 is laminated at another nip and then the final die 132 cuts the product 134 to shape, and cut waste 170 is wound.

It will be understood by those skilled in the art that the schematic diagrams contained in FIGS. 11-12 represent possible equipment configurations only and should not be construed as limiting the method of the present invention.

FIG. 11-12 depict a schematic diagram of web fed rotary processing equipment for producing dressings according to the preferred methods of the present invention. The details of designing such equipment will be well known to those skilled in the art. Commercially available rotary web processing equipment including control depth die cut systems useful for practicing the method of the present invention can be obtained from, for example, the Mark Andy Company (St. Louis, Mo.) and Delta Industrial Services Inc. (Minneapolis, Minn.).

Exemplary embodiments of this invention are discussed and reference has been made to possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the claims provided below and equivalents thereof.

What is claimed is:

1. A medical dressing comprising:
    a backing layer with a first major surface, a second major surface, and an opening through the backing layer to form a window,
    a first adhesive coated on at least a portion of the first major surface,
    a self-supporting substrate comprising
        a first planar surface comprising a corrugated pattern on at least a portion of the first planar surface,
        at least one side wall at an angle between zero to one hundred eighty degrees to the first planar surface, and
        a second planar surface connected to the at least one side wall in the form of a flange,
    a second adhesive adhered to the flange,
    wherein the sidewall has a first periphery proximate the first planar surface and a second periphery proximate the second planar surface,
    wherein the second planar surface is connected to the at least one side wall continuously along the entire second periphery,
    wherein the second adhesive is attached to the backing layer to enclose the window on at least one of the first major surface or second major surface of the backing layer,
    wherein the medical dressing forms a hermetically sealed environment over a wound or other body site.

2. The medical dressing of claim 1, wherein the self supporting substrate is sealed to the backing layer and forms a cavity.

3. The medical dressing of claim 1, wherein the profile of the dressing is at least 5 millimeters.

4. The medical dressing of claim 1, wherein the profile of the dressing is no more than 50 millimeters.

5. The medical dressing of claim 1, further comprising a barrier element and/or a wound packing material.

6. The medical dressing of claim 1, wherein the window is proximate the center of the backing layer.

7. The medical dressing of claim 1, wherein the self-supporting substrate comprises a flexible material.

8. The medical dressing of claim 1, wherein the self-supporting substrate comprises a thermoplastic material, wherein the thermoplastic material is polyethylene.

9. The medical dressing of claim 1, further comprising an absorbent material.

10. The medical dressing of claim 1 wherein the adhesive layer includes at least one medicament comprising an anti-infective agent, an antimicrobial, polyhexamethylene biguanide, chlorhexidine, silver, iodine, iodophor, benzalkonium chloride, hydrogen peroxide, antibiotics, debridement agents, analgesics, healing factors, nitric oxide releasing materials, matrix metalloproteinase inhibitors, vitamins, growth factors, and nutrients.

11. The medical dressing of claim 1, further comprising a wound packing layer.

12. The medical dressing of claim 11, wherein the wound packing layer comprises a foam or resilient nonwoven packing.

13. The medical dressing of claim 1, wherein the self supporting substrate comprises a valve.

14. The medical dressing of claim 1, wherein the corrugated portion comprises alternating ridges and valleys in the planar surface of the self supporting substrate.

15. The medical dressing of claim 1, wherein the self supporting substrate comprises a valve.

* * * * *